US012262945B2

(12) United States Patent
Abitbol et al.

(10) Patent No.: US 12,262,945 B2
(45) Date of Patent: Apr. 1, 2025

(54) VIRTUAL REALITY OCULAR EXAMINATION SYSTEM

(71) Applicant: VISIONIX—LUNEAU TECHNOLOGY, Jerusalem (IL)

(72) Inventors: Marc Abitbol, Jerusalem (IL); Arthur Rabner, Yokneam Ilit (IL)

(73) Assignee: VISIONIX—LUNEAU TECHNOLOGY, Jerusalem (IL)

(*) Notice: Subject to any disclaimer, the term of this patent is extended or adjusted under 35 U.S.C. 154(b) by 755 days.

(21) Appl. No.: 17/422,287

(22) PCT Filed: Jan. 13, 2019

(86) PCT No.: PCT/IL2019/050050
§ 371 (c)(1),
(2) Date: Jul. 12, 2021

(87) PCT Pub. No.: WO2020/144670
PCT Pub. Date: Jul. 16, 2020

(65) Prior Publication Data
US 2022/0071483 A1    Mar. 10, 2022

(51) Int. Cl.
*A61B 3/09* (2006.01)
*A61B 3/00* (2006.01)
(Continued)

(52) U.S. Cl.
CPC .............. *A61B 3/09* (2013.01); *A61B 3/0041* (2013.01); *A61B 3/0091* (2013.01); *G09G 3/001* (2013.01);
(Continued)

(58) Field of Classification Search
CPC ................................ A61B 3/0091; A61B 3/09
See application file for complete search history.

(56) References Cited

U.S. PATENT DOCUMENTS 5,684,561 A * 11/1997 Yancey ................ A61B 3/1208
351/209
7,290,879 B2 * 11/2007 Nagata ................ A61B 3/0091
351/205
(Continued)

FOREIGN PATENT DOCUMENTS

| JP | 2008-55021 A | 3/2008 |
|---|---|---|
| WO | 2008/144168 A2 | 11/2008 |
| WO | 2020/144670 A1 | 7/2020 |

OTHER PUBLICATIONS

Hasegawa, S., et al. (2009). Lens Accommodation to the Stereoscopic Vision on HMD. In: Shumaker, R. (eds) Virtual and Mixed Reality. VMR 2009. Lecture Notes in Computer Science, vol. 5622. Springer, Berlin, Heidelberg. https://doi.org/10.1007/978-3-642-02771-0_49 (Year: 2009).*

(Continued)

*Primary Examiner* — Zachary W Wilkes
(74) *Attorney, Agent, or Firm* — Sughrue Mion, PLLC

(57) ABSTRACT

A virtual reality display system including at least one optical alignment subsystem optically aligned with at least one eye of a subject and at least one virtual reality display device optically aligned with the at least one optical alignment subsystem for displaying to the subject at least one virtual reality object undergoing virtual motion, wherein the virtual motion of the at least one virtual reality object as viewable by the subject is operative for inducing and relaxing accommodation by the at least one eye of the subject.

17 Claims, 19 Drawing Sheets

(51) Int. Cl.
  *A61B 3/028* (2006.01)
  *G02B 27/01* (2006.01)
  *G09G 3/00* (2006.01)
  *A61B 3/02* (2006.01)
  *A61B 3/024* (2006.01)
  *A61B 3/032* (2006.01)
  *A61B 3/06* (2006.01)
  *A61B 3/08* (2006.01)
  *A61B 3/10* (2006.01)
  *A61B 3/18* (2006.01)

(52) U.S. Cl.
  CPC .............. *A61B 3/022* (2013.01); *A61B 3/024* (2013.01); *A61B 3/0285* (2013.01); *A61B 3/032* (2013.01); *A61B 3/063* (2013.01); *A61B 3/066* (2013.01); *A61B 3/08* (2013.01); *A61B 3/085* (2013.01); *A61B 3/1015* (2013.01); *A61B 3/18* (2013.01); *G02B 27/017* (2013.01)

(56) References Cited

U.S. PATENT DOCUMENTS

| | | | | |
|---|---|---|---|---|
| 9,192,296 | B2* | 11/2015 | Abitbol | A61B 3/1005 |
| 9,462,939 | B2 | 10/2016 | Abitbol et al. | |
| 9,504,378 | B2 | 11/2016 | Lee et al. | |
| 9,572,486 | B2* | 2/2017 | Voigtmann | A61B 3/032 |
| 9,844,323 | B2 | 12/2017 | Pamplona et al. | |
| 10,383,513 | B2* | 8/2019 | Abitbol | A61B 3/145 |
| 10,852,551 | B1* | 12/2020 | Sharma | H04N 23/54 |
| 11,793,707 | B2* | 10/2023 | Park | A61B 3/00 |
| 2008/0284979 | A1* | 11/2008 | Yee | A61B 3/103 |
| | | | | 351/205 |
| 2011/0205633 | A1 | 8/2011 | Suzuki et al. | |
| 2015/0042957 | A1* | 2/2015 | Abitbol | A61B 3/1015 |
| | | | | 351/246 |
| 2018/0116505 | A1* | 5/2018 | Abitbol | A61B 3/14 |
| 2018/0136486 | A1 | 5/2018 | Macnamara et al. | |
| 2018/0263488 | A1 | 9/2018 | Pamplona et al. | |
| 2019/0069777 | A1* | 3/2019 | Krall | A61B 3/0091 |
| 2021/0290053 | A1* | 9/2021 | Tran | A61B 3/0091 |

OTHER PUBLICATIONS

Extended European Search Report dated Jul. 27, 2022 in European Application No. 19909204.0.

An Office Action dated Nov. 10, 2022, which issued during the prosecution of Japanese Patent Application No. 2021-540295.

An International Search Report and a Written Opinion both dated May 24, 2019, which issued during the prosecution of Applicant's PCT/IL2019/050050.

An International Preliminary Report on Patentability dated Jun. 16, 2021, which issued during the prosecution of Applicant's PCT/IL2019/050050.

* cited by examiner

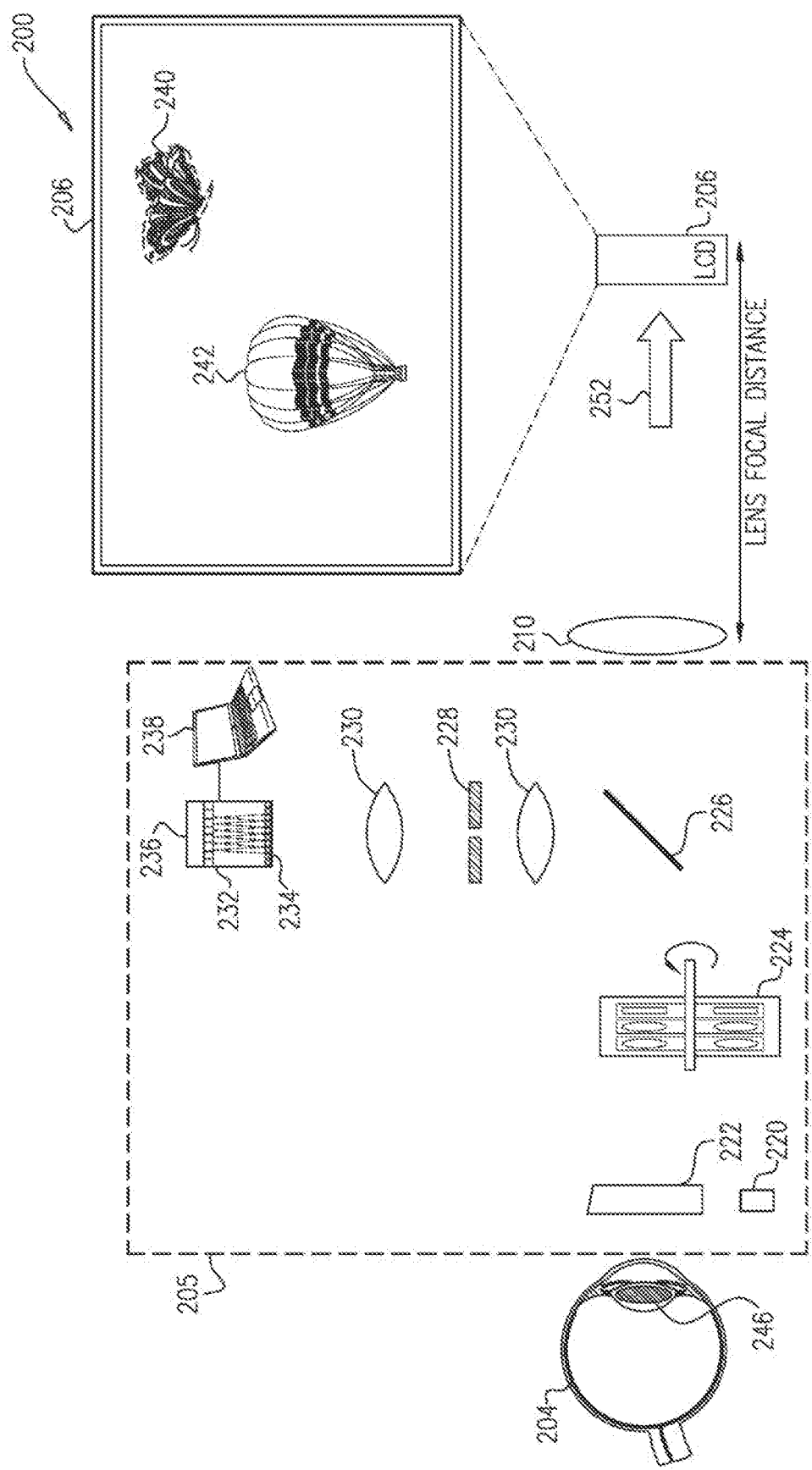

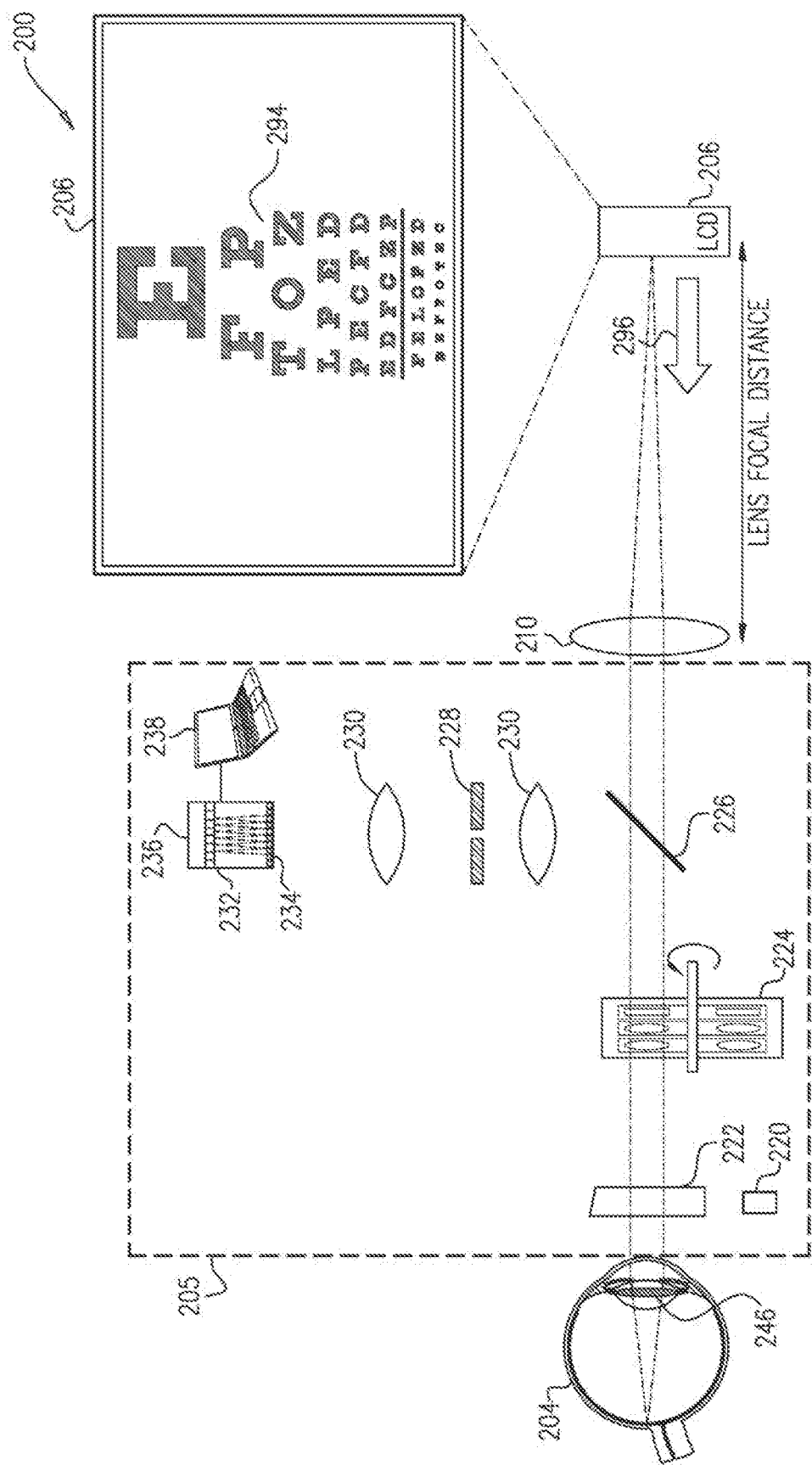

VIRTUAL REALITY OCULAR EXAMINATION SYSTEM

RELATED APPLICATIONS

Reference is hereby made to U.S. Pat. No. 9,462,939, filed Apr. 4, 2013, and to U.S. patent application Ser. No. 15/982,259, filed May 17, 2018, both entitled OBJECTIVE PHOROPTER SYSTEM, the disclosures of which are hereby incorporated by reference.

FIELD OF THE INVENTION

The present invention relates generally to ocular examination systems and more particularly to ocular examination systems employing virtual reality displays.

BACKGROUND OF THE INVENTION

Various types of ocular examination systems employing virtual reality displays are known in the art.

SUMMARY OF THE INVENTION

The present invention seeks to provide improved ocular examination systems and methods employing virtual reality displays useful for inducing and relaxing accommodation of the eye of a subject.

There is thus provided in accordance with a preferred embodiment of the present invention a virtual reality display system including at least one optical alignment subsystem optically aligned with at least one eye of a subject and at least one virtual reality display device optically aligned with the at least one optical alignment subsystem for displaying to the subject at least one virtual reality object undergoing virtual motion, wherein the virtual motion of the at least one virtual reality object as viewable by the subject is operative for inducing and relaxing accommodation by the at least one eye of the subject.

There is additionally provided in accordance with another preferred embodiment of the present invention an ocular examination system including at least one optical alignment subsystem optically aligned with at least one eye of a subject, at least one virtual reality display device optically aligned with the at least one optical alignment subsystem for displaying to the subject at least one virtual reality object undergoing virtual motion, wherein the virtual motion of the at least one virtual reality object as viewable by the subject is operative for inducing and relaxing accommodation by the at least one eye of the subject and an ocular testing subsystem for use in performing a visual test on the subject following the relaxing of accommodation by the subject.

Preferably, the virtual reality display device is physically moveable along at least one axis, physical motion of the virtual reality display device along the at least one axis complementing the virtual motion of the at least one virtual reality object.

Preferably, the virtual motion of the at least one virtual reality object includes at least one of receding motion, advancing motion, change in at least one of a size and position of the virtual reality object, change in at least one of a size and position of the at least one virtual reality object with respect to another virtual reality object on the virtual reality display device, blurring of the virtual reality object as perceivable by the subject and improving clarity of the virtual reality object as perceivable by the subject.

Preferably, the system also includes a light collimating element interfacing the virtual reality display device and the optical alignment subsystem for collimating light emanating from the virtual reality display device.

In accordance with a preferred embodiment of the present invention, the system includes a binocular system.

In accordance with another preferred embodiment of the present invention, the ocular testing subsystem includes at least one of an objective testing subsystem and a subjective testing subsystem.

Preferably, the visual test includes at least one of a prismatic measurement, a field perimeter measurement, a three-dimensional vision test, a color vision test, a contrast sensitivity test, a vision acuity in motion test, a night vision test, a monocular amplitude of accommodation test, a CA/C and AC/A ratio test, a strabismus test, and a pupillary response test.

Preferably, the ocular testing subsystem includes a combined phoropter and auto-refraction device.

Preferably, the ocular testing subsystem includes a visual acuity testing subsystem and the virtual reality object includes a virtual reality visual acuity testing target displayed on the virtual reality display device.

Preferably, the virtual reality visual acuity testing target includes a Snellen chart.

There is furthermore provided in accordance with yet another preferred embodiment of the present invention a method for performing an ocular examination on a subject including optically aligning at least one virtual reality display device with at least one eye of a subject, displaying to the subject at least one virtual reality object on the virtual reality display device, creating virtual motion of the at least one virtual reality object as viewable by the subject, thereby inducing and relaxing accommodation by the at least one eye of the subject and performing at least one visual test on the subject following the relaxing of accommodation by the subject.

Preferably, the at least one visual test includes at least one of an objective visual test and a subjective visual test.

Preferably, the at least one visual test includes at least one of a prismatic measurement, a field perimeter measurement, a three-dimensional vision test, a color vision test, a contrast sensitivity test, a vision acuity in motion test, a night vision test, a monocular amplitude of accommodation test, a CA/C and AC/A ratio test, a strabismus test, and a pupillary response test.

Preferably, at least one visual test includes a combined subjective phoropter test and object wavefront analysis test.

Preferably, the at least one visual test includes a visual acuity test and the virtual reality object includes a virtual reality visual acuity testing target displayed on the virtual reality display device.

Preferably, the virtual reality visual acuity testing target includes a Snellen chart.

Preferably, the method also includes physically moving the virtual reality display device along at least one axis of motion, physical motion of the virtual reality display device along the at least one axis complementing the virtual motion of the at least one virtual reality object.

Preferably, the virtual motion of the at least one virtual reality object includes at least one of receding motion, advancing motion, change in at least one of a size and position of the virtual reality object, change in at least one of a size and position of the at least one virtual reality object with respect to another virtual reality object on the virtual reality display device, blurring of the virtual reality object as perceivable by the subject and improving clarity of the virtual reality object as perceivable by the subject.

Preferably, the method also includes collimating light emanating from the virtual reality display device prior to the light arriving at the eye of the subject.

BRIEF DESCRIPTION OF THE DRAWINGS

The present invention will be understood and appreciated more fully based on the following detailed description taken in conjunction with the drawings in which:

FIGS. 2A-2J are simplified schematic illustrations of an optical examination device including a virtual reality display system, respectively illustrating a series of virtual reality display screens displayed to a subject for inducing and relaxing accommodation during the performance of an optical examination on the subject, constructed and operative in accordance with another preferred embodiment of the present invention;

DETAILED DESCRIPTION OF PREFERRED EMBODIMENTS

Figure 1A:
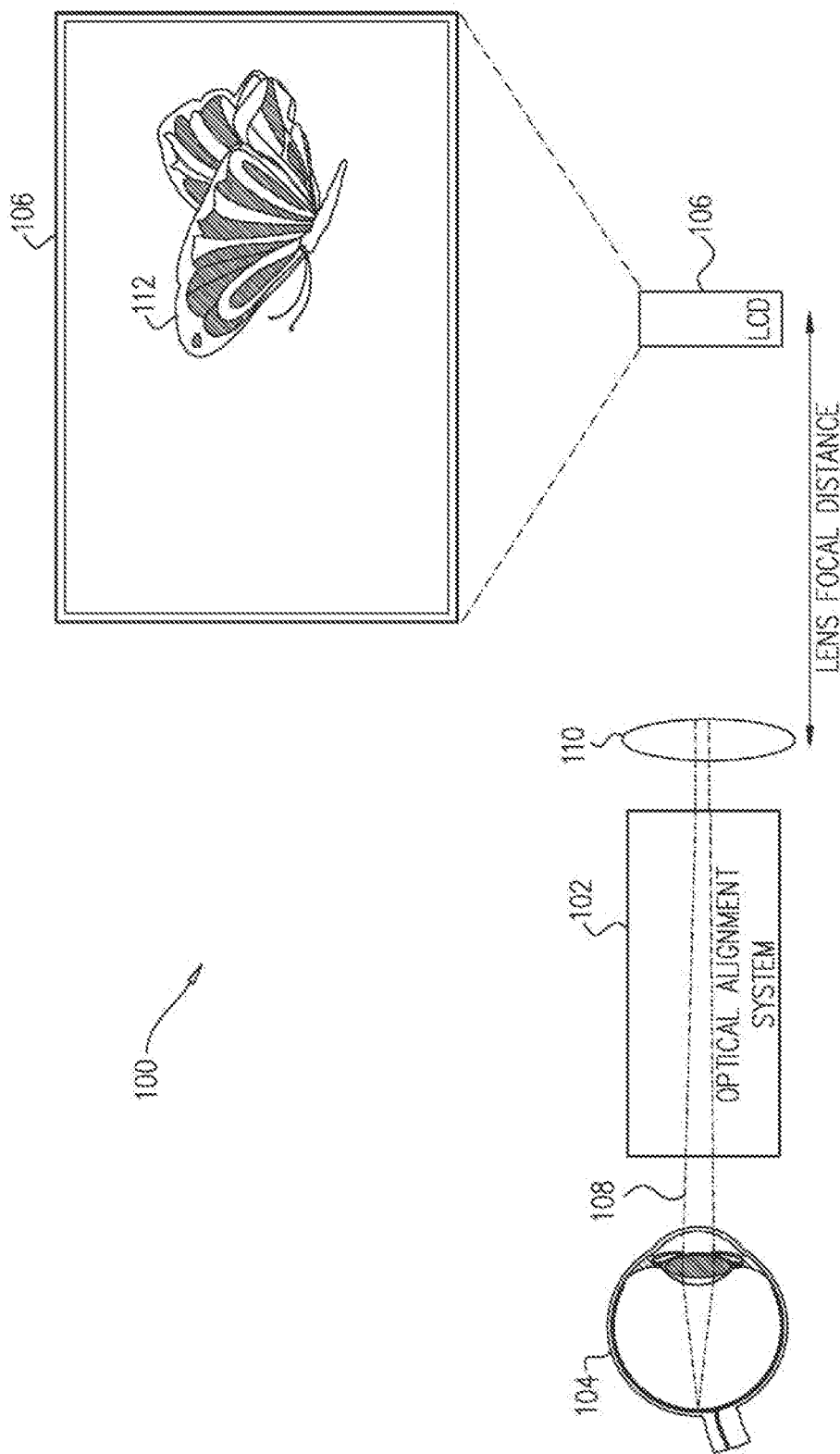
FIGS. 1A-1E are simplified schematic illustrations of a virtual reality display system, respectively illustrating a series of virtual reality display screens displayed to a subject for inducing and relaxing accommodation of an eye of the subject, constructed and operative in accordance with a preferred embodiment of the present invention.

Reference is now made to FIGS. 1A-1E, which are simplified schematic illustrations of a virtual reality display system, illustrating a series of virtual reality display screens displayed to a subject for inducing and relaxing accommodation of an eye of the subject, constructed and operative in accordance with a preferred embodiment of the present invention.

As seen in FIGS. 1A-1E, there is provided a virtual reality display system 100, including at least one optical alignment subsystem, here embodied as an optical alignment subsystem 102, optically aligned with at least one eye 104 of a viewer, and at least one virtual reality display device, here embodied, by way of example, as a virtual reality display screen 106. Virtual reality display screen 106 is preferably optically aligned with optical alignment subsystem 102 and thus correspondingly optically aligned with eye 104 of the viewer. Optical alignment subsystem 102 may be any optical component or components for facilitating optical alignment of eye 104 with display screen 106 including, but not limited to, a transparent body having optical properties for suitably refracting light rays 108 entering eye 104. By way of example, optical alignment subsystem 102 may include a standard set of phoropter wheels, a variable focal length liquid lens or a variable focus liquid crystal device. In a particularly preferred embodiment of the present invention, optical alignment subsystem 102 includes one or more wheels of phoropter lenses of a phoropter device, as is detailed henceforth with reference to FIGS. 2A-2J.

System 100 further preferably includes a light collimating structure, here embodied, by way of example, as a collimating lens 110. Collimating lens 110 is preferably located interfacing display screen 106 and optical alignment subsystem 102 and preferably is functional to collimate incoming light emanating from display screen 106, which collimated incoming light then preferably propagates towards optical alignment subsystem 102 and therethrough to eye 104.

Virtual reality display screen 106 is preferably adapted for displaying to eye 104 of the viewer at least one virtual reality object, here shown to be embodied as a butterfly 112. It is appreciated that virtual reality display screen 106 is shown in side view in FIGS. 1A-1E, with an enlarged frontal view of virtual reality display screen 106 displayed thereabove.

FIG. 1A shows an initial state of system 100, in which virtual reality display screen 106 is axially aligned with eye 104 and optical alignment subsystem 102 and axially separated from collimating lens 110 by a distance generally equal to the focal distance of collimating lens 110. Eye 104 preferably views butterfly 112 displayed on display screen 106 via optical alignment subsystem 102 and collimating lens 110.

It is appreciated that although system 100 is illustrated in FIGS. 1A-1E as comprising a single display screen 106 displaying a virtual reality object to one eye, namely eye 104, of the viewer, this is for simplicity and clarity of representation only. System 100 is preferably, although not necessarily, formed as a binocular system, including two individual screens each of a type resembling display screen 106, each screen being aligned with one eye of a viewer. A similar or identical virtual reality object, such as butterfly 112, is preferably simultaneously displayed on both screens at such a position on the individual screens that the two eyes of the viewer perceive the two virtual reality objects as a single object.

Figure 1B:
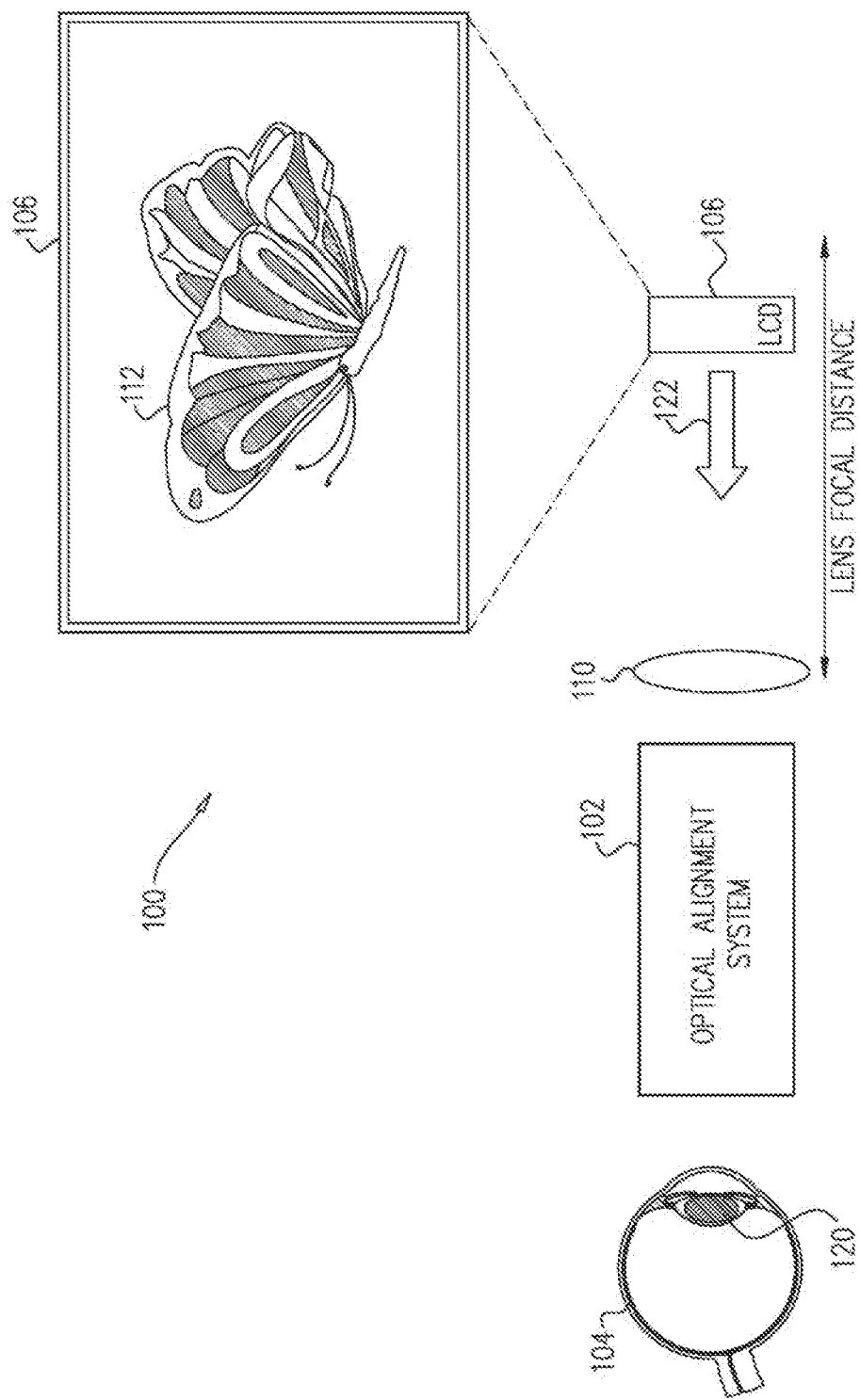

FIG. 1B shows a subsequent state of system 100, which subsequent state preferably follows the initial state of system 100 illustrated in FIG. 1A. As appreciated from consideration of the appearance of screen 106 in FIG. 1A in comparison to that in FIG. 1B, butterfly 112 has undergone virtual motion in the progression from FIG. 1A to FIG. 1B, so as to move to a new position on screen 106 in FIG. 1B. Here, by way of example, butterfly 112 is seen to be enlarged in FIG. 1B compared to FIG. 1A and to have moved in a nasal direction, towards the nose of the viewer, which in this case is shown as movement in a direction towards the center of screen 106. It is appreciated that the direction of nasal movement may be in the opposite direction to that shown, depending on whether 104 is the left or right eye of the viewer. Such virtual motion of butterfly 112 as viewed by eye 104 of a viewer serves to create an impression that butterfly 112 is approaching the viewer and thus induces accommodation by eye 104 viewing butterfly 112. As seen in FIG. 1B, a lens 120 of eye 104 is shown to become thicker and shorter due to the induction of accommodation as a result of the perception by eye 104 of butterfly 112 becoming closer thereto.

The perception by eye 104 of butterfly 112 approaching the viewer is preferably enhanced by way of axial movement of screen 106 towards collimating lens 110, along a direction indicated by an arrow 122, such that screen 106 is located closer to collimating lens 110 than the focal distance thereof.

Such movement of screen 106 preferably serves to enhance the perception of butterfly 112 as approaching the viewer. Furthermore, such movement of screen 106 towards eye 104 tends to cause blurring of butterfly 112 as perceived by eye 104, thus further encouraging accommodation by eye 104.

In certain embodiments of the present invention, axial movement of screen 106 towards collimating lens 110 may be optionally accompanied by tilting of screen 106 in a nasal direction, in order to further encourage accommodation by eye 104. Such tilting may be performed by tilt motors coupled to screen 106 and/or optical alignment system 102, as is illustrated and described hereinbelow with reference to FIGS. 4A and 4B.

It is appreciated that the virtual motion of butterfly 112 on screen 106 is thus preferably complemented by the physical motion of screen 106 so as to augment the apparent motion of butterfly 112 towards eye 104 and thus more effectively induce accommodation by eye 104. It is understood, however, that the physical motion of screen 106 may alternatively be obviated and the perception of butterfly 112 approaching eye 104 induced solely by way of virtual motion of butterfly 112 on screen 106.

Figure 1C:
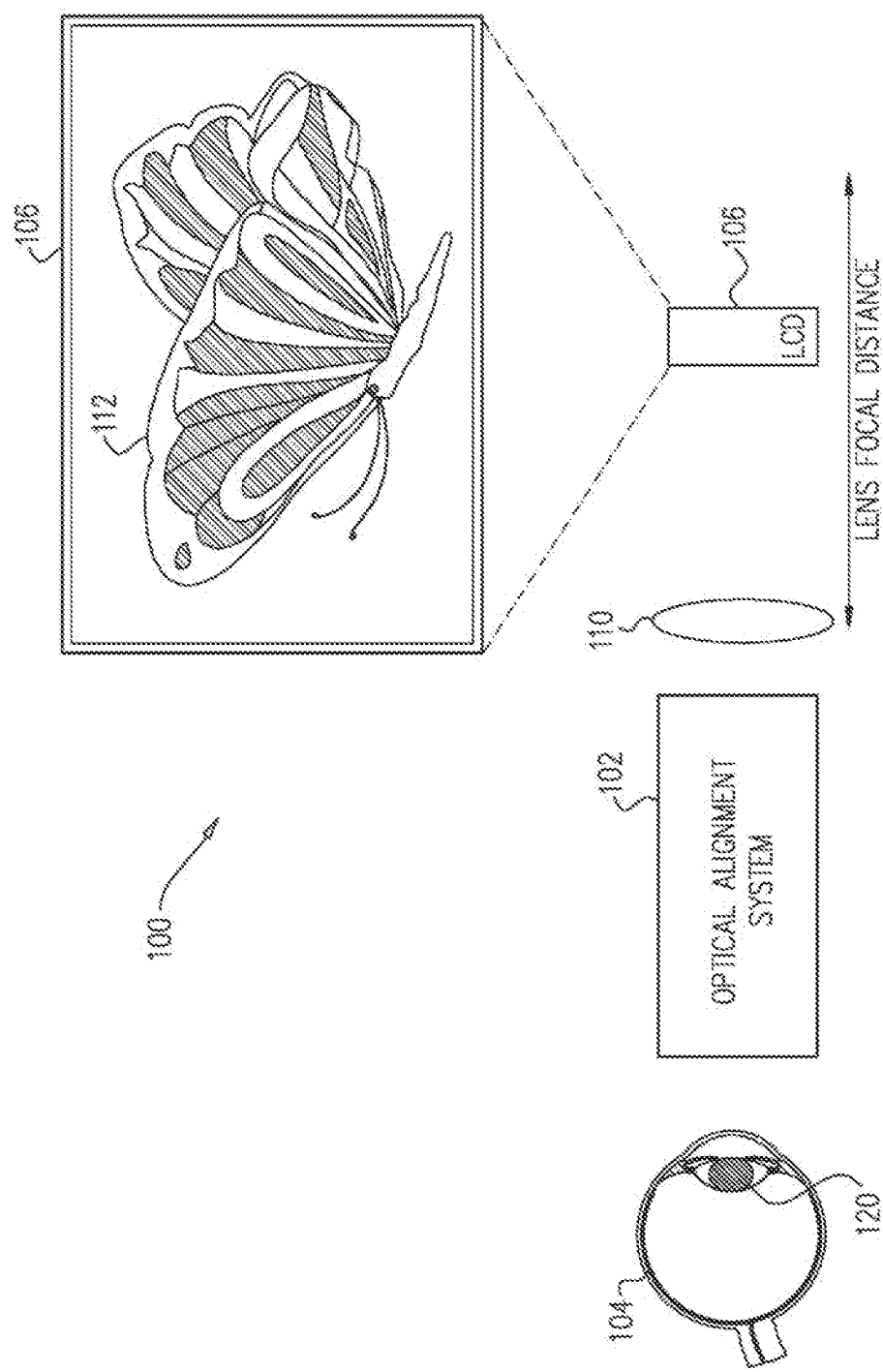

FIG. 1C shows a further subsequent state of system 100, which subsequent state preferably follows the state of system 100 illustrated in FIG. 1B. As appreciated from consideration of the appearance of screen 106 in FIG. 1B in comparison to that in FIG. 1C, butterfly 112 has undergone yet further virtual motion in the progression from FIG. 1B to FIG. 1C, so as to move to a new position on screen 106 in FIG. 1C. Here, by way of example, butterfly 112 is seen to be further enlarged in FIG. 1C compared to FIG. 1B and to have further moved in a nasal direction towards the center of screen 106. Such virtual motion of butterfly 112 as viewable by eye 104 of a viewer serves to create an impression that butterfly 112 is further nearing the viewer and thus further induces accommodation by eye 104 viewing butterfly 112. As seen in FIG. 1C, lens 120 becomes even thicker and shorter due to the further induction of accommodation as a result of the perception by eye 104 of butterfly 112 becoming nearer to eye 104.

Figure 1D:
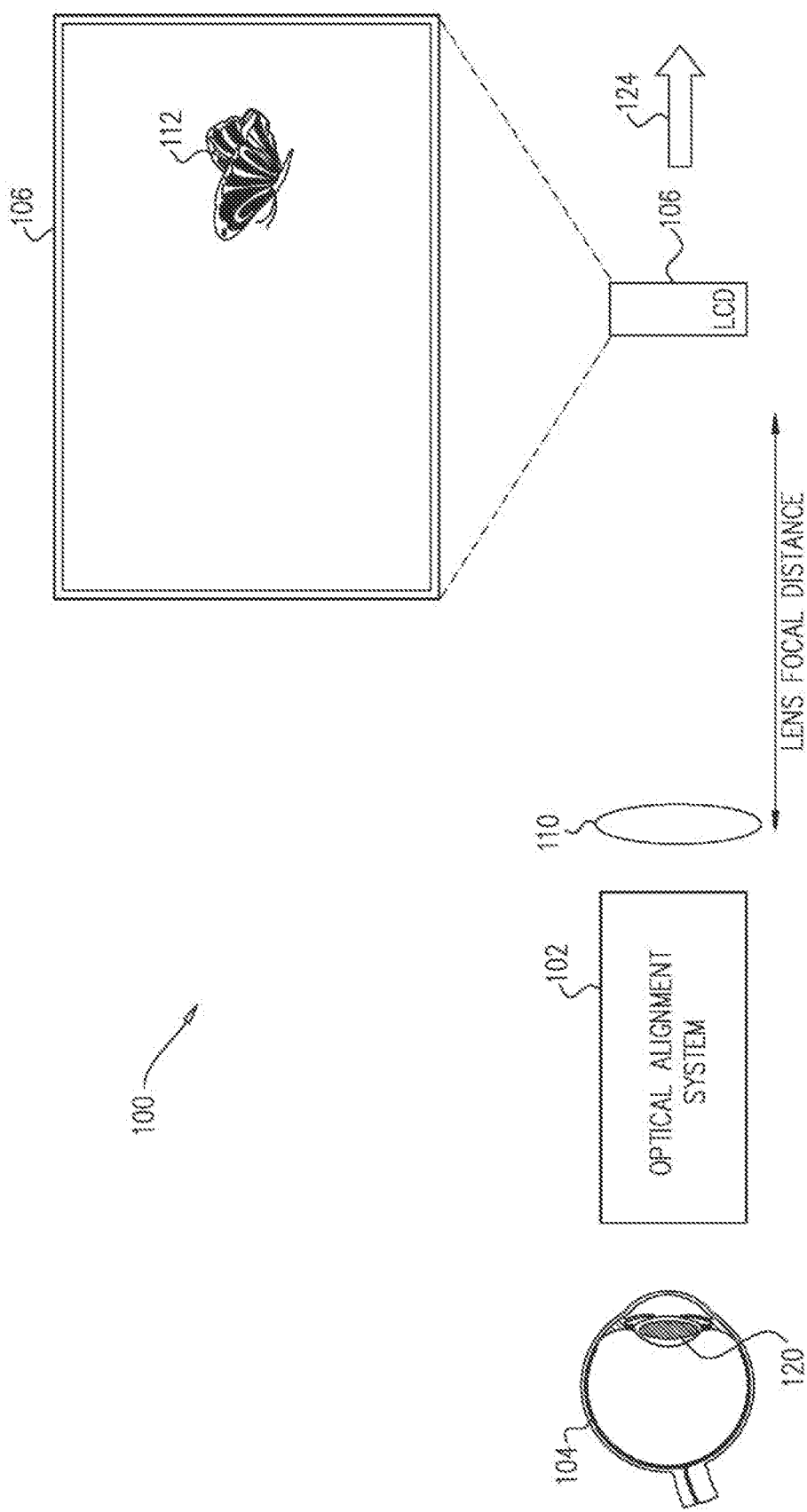

FIG. 1D shows a further subsequent state of system 100, which subsequent state preferably follows the state of system 100 illustrated in FIG. 1C. As appreciated from consideration of the appearance of screen 106 in FIG. 1D in comparison to that in FIG. 1C, butterfly 112 has undergone yet further virtual motion in the progression from FIG. 1C to FIG. 1D, so as to assume a new position on screen 106 in FIG. 1D. Here, by way of example, butterfly 112 is seen to be reduced in size as in FIG. 1D compared to FIG. 1C and to have moved in a temporal direction, away from the nose of the viewer, which in this case is exhibited as movement away from the center of screen 106. It is appreciated that the direction of temporal movement may be in the opposite direction to that shown, depending on whether 104 is the left or right eye of the viewer. Such virtual motion of butterfly 112 as viewable by eye 104 of a viewer serves to create an impression that butterfly 112 is now receding from the viewer and thus initiates relaxation of accommodation by lens 120 of eye 104 viewing butterfly 112. As seen in FIG. 1D, lens 120 becomes thinner and longer due to the relaxation of accommodation as a result of the perception by eye 104 of butterfly 112 becoming further away from eye 104.

The perception by eye 104 of butterfly 112 becoming more remote from the viewer is preferably enhanced by way of axial movement of screen 106 away from collimating lens 110, along a direction indicated by an arrow 124, such that screen 106 is located axially beyond the focal distance of collimating lens 110. Such movement of screen 106 preferably serves to enhance the perception of butterfly 112 as receding from the viewer and thus encourages relaxation of accommodation by eye 104. Butterfly 112 would typically be perceived as blurred by eye 104 in the arrangement illustrated in FIG. 1D, due to the location of screen 106 at a point beyond the focal distance of collimating lens 110 and the inability of eye 104 to compensate for the blur by accommodating.

It is appreciated that the virtual motion of butterfly 112 on screen 106 is thus complemented by the physical motion of screen 106 so as to augment the apparent motion of butterfly 112 away from eye 104 and thus more effectively relax accommodation by eye 104.

It is understood, however, that the physical motion of screen 106 may alternatively be obviated and the perception of butterfly 112 as receding from eye 104 induced solely by way of virtual motion of butterfly 112 on screen 106.

Figure 1E:
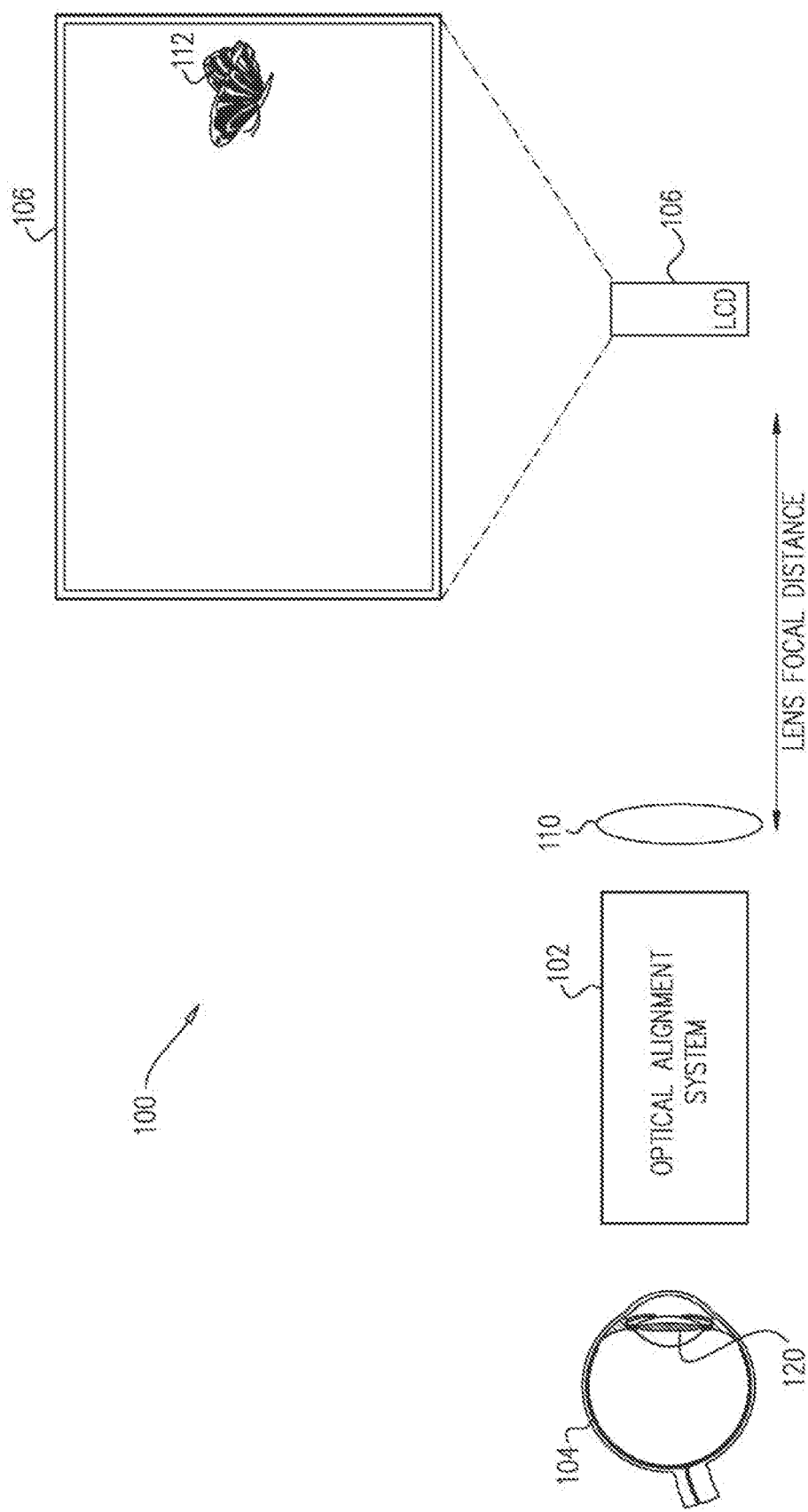

FIG. 1E shows a further subsequent state of system 100, which subsequent state preferably follows the state of system 100 illustrated in FIG. 1D. As appreciated from consideration of the appearance of screen 106 in FIG. 1E in comparison to that in FIG. 1D, butterfly 112 has undergone yet further virtual motion in the progression from FIG. 1D to FIG. 1E, so as to assume a new position on screen 106 in FIG. 1D. Here, by way of example, butterfly 112 is seen to be reduced in size in FIG. 1E compared to FIG. 1D and to have further moved in a temporal direction, in this case shown as away from the center of screen 106. Such virtual motion of butterfly 112 as viewable by eye 104 of a viewer serves to create an impression that butterfly 112 is further receding from the viewer and thus further promotes relaxation of accommodation by lens 120 of eye 104 viewing butterfly 112.

It is appreciated that there is preferably no change in position of screen 106 between FIGS. 1D and 1E. Screen 106 and hence butterfly 112 displayed thereon is preferably located at a point beyond the focal distance of collimating lens 110 in both FIGS. 1D and 1E, such that lens 120 may be expected to be in a non-accommodative state in both FIGS. 1D and 1E. However, the continued motion of butterfly 112 in FIG. 1E preferably serves to prolong tracking of butterfly 112 by eye 104 of a viewer, such that the viewer becomes immersed in the virtual environment provided by screen 106 and thus genuinely feels and perceives butterfly 112 as a distant object and fully relaxes accommodation accordingly. Such immersion in the virtual environment provided by screen 106 is significant, since in the case that the viewer remains aware that the virtual reality object, such as butterfly 112, is not truly distant but rather is simply being displayed as such, this awareness by the viewer may influence the extent of accommodation by eye 104 and prevent full relaxation of accommodation. As seen in FIG. 1E, further motion of butterfly 112 causes lens 120 to continue to assume a thinner and longer shape in comparison to that shown in FIG. 1D, due to the further relaxation of accommodation thereby as a result of the perception by eye 104 of butterfly 112 becoming yet further away from eye 104.

It is appreciated that the direction of gradual movement of butterfly 112 in FIGS. 1A through to 1C in a nasal direction, in this case exhibited as a direction towards the center of screen 106 in order to induce accommodation by eye 104 is preferably opposite to the temporal direction of gradual movement of butterfly 112 in FIGS. 1C-1E, in order to reverse the perception of motion of butterfly 112 by the viewer. However, it is understood that the particular direction of motion shown as corresponding to nasal and temporal directions is exemplary only and may alternatively be reversed between FIGS. 1A-1C and FIGS. 1C-1E, depending on whether eye 104 is the left or right eye of the viewer.

It is additionally understood that the virtual motion of butterfly 112 on screen 106, so as to induce and subsequently relax accommodation by eye 104 of a viewer viewing screen 106, is illustrated in discrete steps in FIGS. 1A-1E for ease of representation only and that in actuality, the progression of virtual motion of butterfly 112 is preferably, although not necessarily, continuous so as to create an impression of butterfly 112 flying towards or away from the viewer.

It is further understood that although the virtual motion of butterfly 112 is ordered in the progression from FIGS. 1A-1E so as to induce and subsequently relax accommodation by eye 104, the sequence of virtual motion of butterfly 112 and the corresponding optional physical motion of screen 106 may alternatively be reversed, so as to deliberately relax and subsequently induce accommodation by eye 104, depending on the function of system 100.

It is appreciated that the inclusion of optical alignment subsystem 102 in system 100 is particularly advantageous, since eye 104 is preferably thereby optically aligned with display screen 106 before the initiation of virtual motion of butterfly 112. This is in contrast to conventional virtual reality display systems, in which the eye of the viewer is not necessarily optically aligned with the virtual reality display. Additionally, because system 100 may provide a relatively narrow field of view (FOV) of virtual reality screen 106 through optical alignment subsystem 102, in comparison to conventional virtual reality display systems typically having a far wider FOV, screen-door effects are advantageously reduced in system 100, allowing the viewer to clearly perceive virtual reality images such as butterfly 112 on virtual reality display screen 106 without disturbing pixilation effects. It is appreciated, however, that in certain embodiments of the present invention, it may be advantageous for optical alignment system 102 to provide a wider FOV of virtual reality screen 106, for example for field of view testing, as described hereinbelow.

Induced changes in the near and far distance perception by a viewer of a virtual reality object as a result of virtual motion thereof, leading to corresponding induction and relaxation of accommodation by the eye of the viewer, as provided in accordance with preferred embodiments of the present invention, may be particularly useful in the performance of optical tests in which accommodation by the eye of a subject being tested must be controlled in order to ensure accurate test results.

The inclusion of a virtual reality display system within an exemplary optical examination system, constructed and operative in accordance with a preferred embodiment of the present invention, is now described with reference to FIGS. 2A-2J.

Reference is now made to FIGS. 2A-2J, which are simplified schematic illustrations of an optical examination device including a virtual reality display system, illustrating a series of virtual reality display screens displayed to a subject for inducing and relaxing accommodation during the performance of an optical examination on the subject, constructed and operative in accordance with another preferred embodiment of the present invention.

Figure 2A:
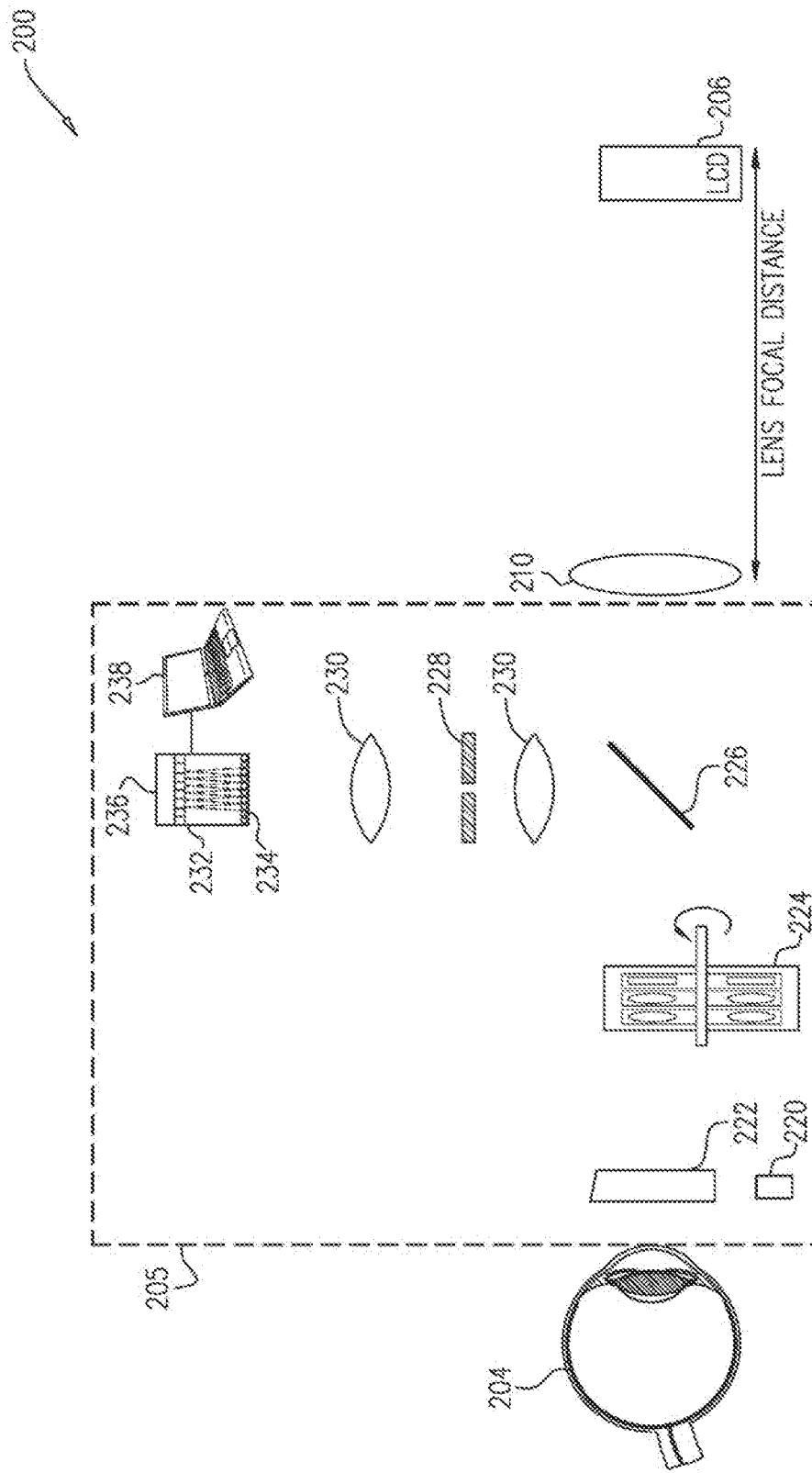

As seen in FIG. 2A, there is provided an ocular examination system 200 for testing an eye 204 of a subject. Ocular examination system 200 preferably includes an ocular testing subsystem 205 optically aligned with at least one virtual reality display device, here embodied, by way of example, as a virtual reality display screen 206 coupled to a collimating lens 210. It is appreciated that virtual reality display screen 206 is shown in side view in FIGS. 2A-2J, with an enlarged frontal view of virtual reality display screen 206 displayed thereabove in FIGS. 2B-2J.

In accordance with a particularly preferred embodiment of the present invention illustrated in FIGS. 2A-2J, ocular testing subsystem 205 is embodied as a combined phoropter/wavefront analysis testing system 205, preferably of the type described in U.S. Pat. No. 9,462,939, assigned to the same assignee as the present invention, the entirety of which is incorporated herein by reference. It is appreciated, however, that ocular testing subsystem 205 may alternatively be embodied as other types of ocular testing subsystems benefitting from integration of a virtual reality display device therewith, including visual acuity testing systems and other types of ocular measurement and screening systems.

Combined phoropter/wavefront analysis testing system 205 is preferably operative for performing combined subjective phoropter and objective refractive measurements for ascertaining aberrations present in eye 204. In one preferred embodiment of the present invention, combined phoropter/wavefront analysis testing system 205 preferably comprises a collimated light source, here embodied by way of example as a laser 220, for illuminating eye 204. Light from laser 220 is preferably directed towards eye 204 by way of a specially shaped quasi-wedged beam splitter 222, as described in U.S. Pat. No. 9,462,939. Light subsequently reflected from eye 204 preferably propagates through the various optical structures of eye 204 and returns to beam splitter 222, wherethrough the reflected light travels towards the lens wheels of a phoropter 224. The light may then be directed away from the direct line of sight of eye 204, preferably by way of an additional beam splitter 226, towards a pin-hole beam aperture 228 preferably disposed between a pair of focusing lenses 230. Light focused through pin-hole beam aperture 228 is preferably directed towards a Shack-Hartmann sensor 232. Shack-Hartmann sensor 232 preferably includes a lenslet array 234 and a detector 236. Lenslet array 234 is preferably operative to focus the incoming light onto detector 236, allowing detection and extraction of a refractive map of eye 204, which refractive map may be displayed, stored or otherwise handled by a computing device 238, preferably connected to Shack-Hartmann sensor 232.

Display screen 206 is preferably disposed in the direct line of sight of eye 204 through additional beam splitter 226 and collimating lens 210. It is appreciated that additional beam splitter 226 in combination with collimating lens 210 and phoropter 224 preferably form components of a preferred embodiment of an optical alignment subsystem, for optically aligning display screen 206 with eye 204 of a subject. Preferably, system 200 includes a series of motors for aligning testing system 205 to eye 204 in vertical and horizontal directions, as well as to bring testing system 205 into a required focus position, thus ensuring that display screen 206 is optically aligned with eye 204.

Display screen 206 is preferably optically aligned with eye 204 for displaying to eye 204 at least one virtual reality object undergoing virtual motion, wherein the virtual motion of the at least one virtual reality object as viewable by eye 204 is operative for inducing and relaxing accommodation by eye 204, preferably prior to performance of the objective refraction measurement by Shack-Hartmann sensor 232 as well as prior to performance of a subjective visual test using phoropter 224, as is detailed henceforth with reference to FIGS. 2B-2I.

Display screen 206 is preferably additionally operative to display to eye 204 a virtual target for use in the subjective aspects of the phoropter measurements by phoropter 224, which virtual target is preferably directly visible through beam splitter 226 and collimating lens 210, as is detailed henceforth with reference to FIG. 2J.

It is understood that the particular configurations of the Shack-Hartmann and phoropter optical systems illustrated and described herein are exemplary only and that ocular testing subsystem 205 may be embodied as any suitable objective and/or subjective refractive testing subsystem, as may be known in the art.

It is further appreciated that the optical alignment of screen 206 with eye 204 is particularly advantageous and is in contrast to conventional virtual reality display systems, in which the eye of the viewer is not necessarily optically aligned with the virtual reality display. Additionally, because system 200 provides a relatively narrow field of view (FOV) of virtual reality screen 206 through phoropter 224, beam splitter 226 and collimating lens 210, in comparison to conventional virtual reality display systems typically having a far wider FOV, screen-door effects are advantageously reduced in system 200, allowing the viewer to clearly perceive virtual reality images on virtual reality display screen 206 without disturbing pixilation effects. It is appreciated, however, that in certain embodiments of the present invention, it may be advantageous to configure testing system 205 and collimating lens 210 so as to provide a wider FOV of virtual reality screen 206, for example for field of view testing, as described hereinbelow.

Figure 2B:
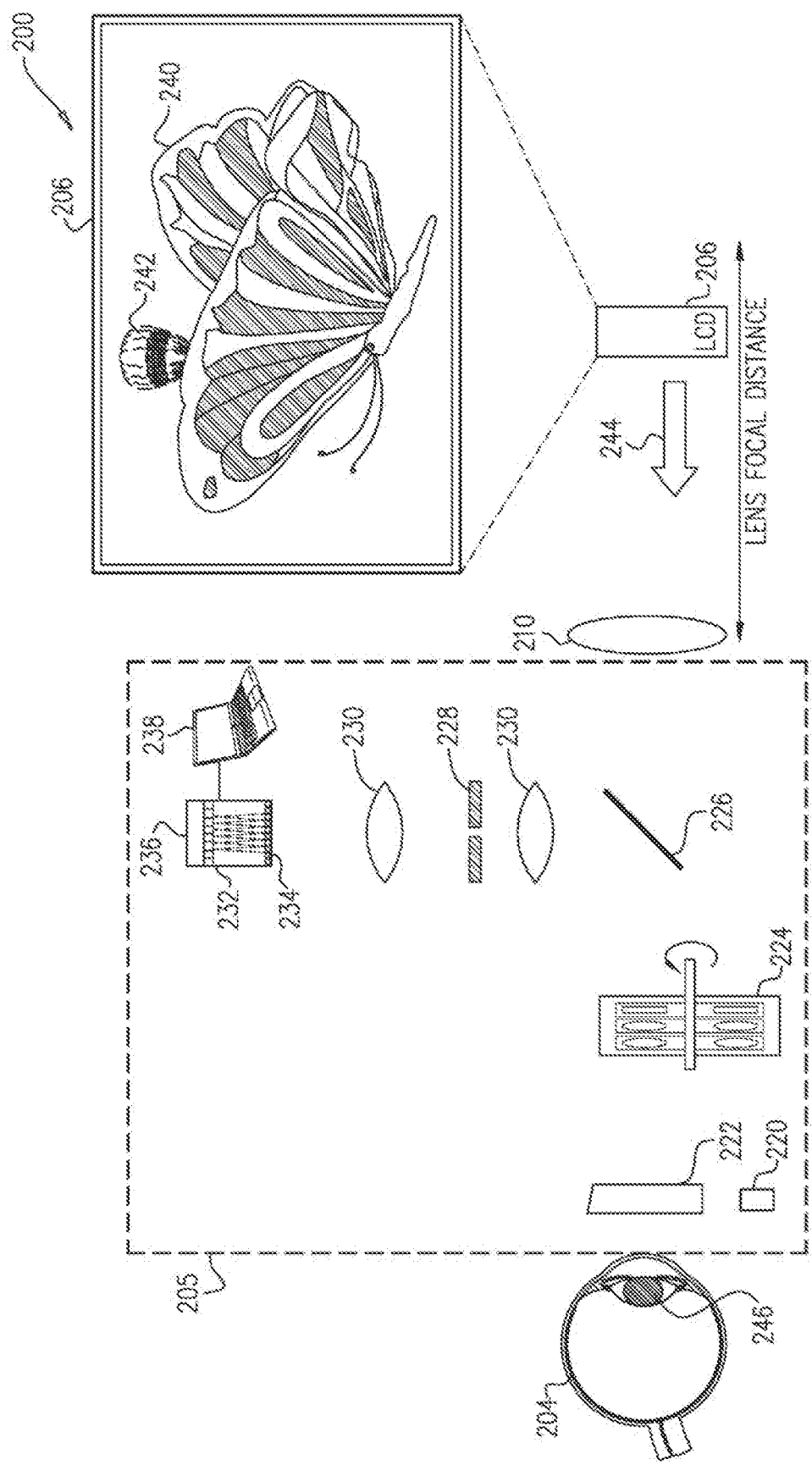

Turning now to FIG. 2B, an initial state of system 200 is shown in which a first virtual reality object such as a butterfly 240 is shown in the forefront of display screen 206 and a second virtual reality object such as a balloon 242 is shown blurred in the background of display screen 206. Here, display screen 206 is shown to be preferably located closer to collimating lens 210 than the focal distance thereof, movement of display screen 206 being indicated by an arrow 244, in order to enhance the perception by eye 204 of butterfly 240 being a close object. Accommodation by a lens 246 of eye 204 is preferably induced due to the perception of butterfly 240 as a close object, as represented by the thickened, shortened state of lens 246 shown in FIG. 2B. Blurring of the apparently more distant balloon 242 serves to enhance the focus of eye 204 on the apparently close and more clearly displayed butterfly 240. It is understood that the state of system 200 illustrated in FIG. 2B corresponds to a state of system 200 prior to the performance of objective or subjective testing of eye 204 thereby.

FIG. 2C shows a subsequent state of system 200, which subsequent state preferably follows the initial state of system 200 illustrated in FIG. 2B. As appreciated from consideration of the appearance of screen 206 in FIG. 2C in comparison to that in FIG. 2B, butterfly 240 and balloon 242 have preferably undergone virtual motion in the progression from FIG. 2B to FIG. 2C, so as to move to respective new positions on screen 206 in FIG. 2C. Here, by way of example, butterfly 240 is seen to be reduced in size in FIG. 2C compared to FIG. 2B and to have moved in a temporal direction, in this case exhibited as a direction away from the center of screen 206. Preferably although not necessarily concurrent with the virtual motion of butterfly 240, balloon 242 is seen to be enlarged and to have moved in a nasal direction, here shown as corresponding to movement towards the forefront and center of screen 206 in FIG. 2C compared to FIG. 2B, such that balloon 242 preferably becomes the object of focus by eye 204. Butterfly 240 is preferably shown as blurred whereas balloon 242 is preferably displayed clearly on screen 206, in order to promote focus by eye 204 on balloon 242. Screen 206 is preferably located at the focus position of lens 210, movement of screen 206 being indicated by an arrow 252.

Figure 2D:
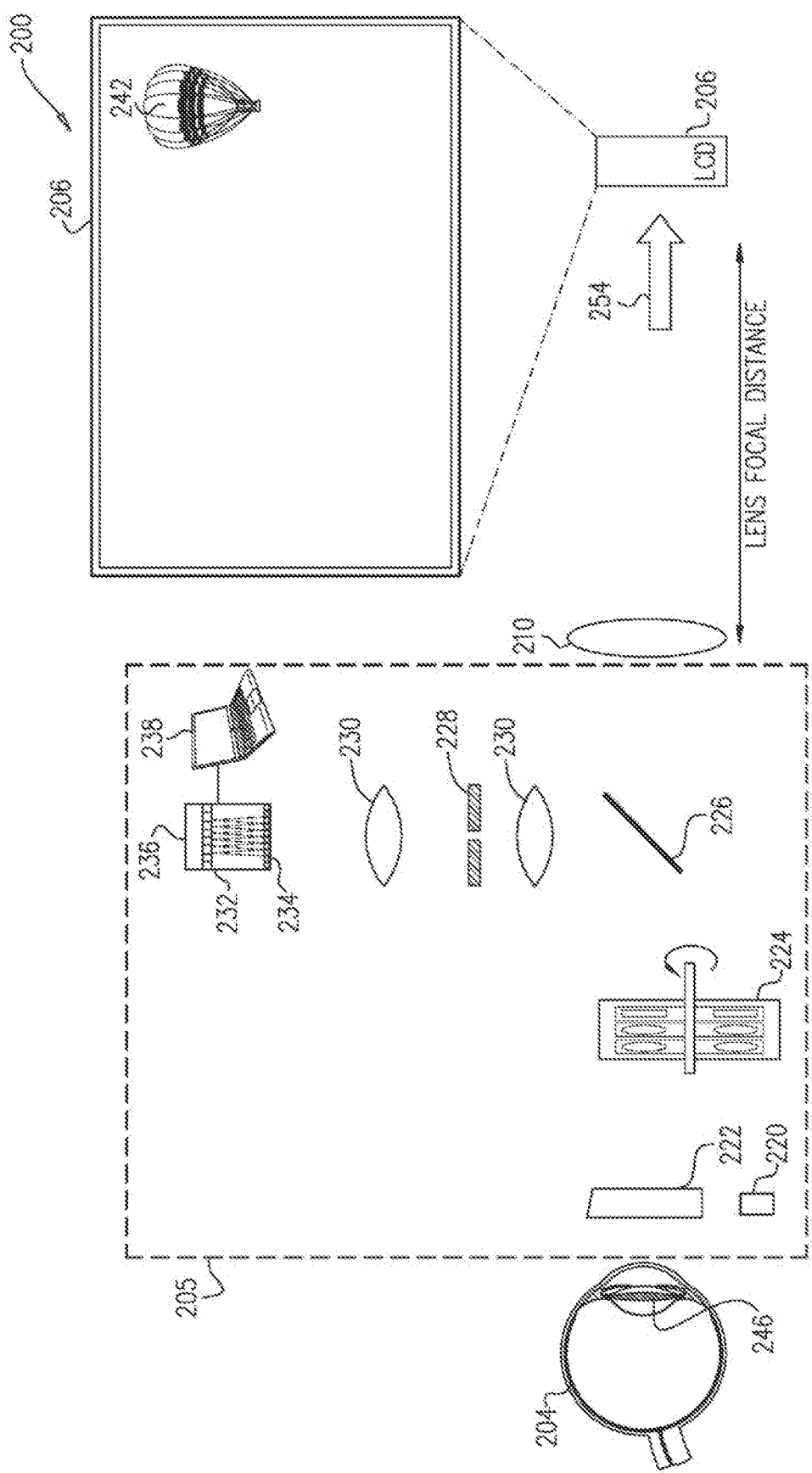

FIG. 2D shows a subsequent state of system 200, which subsequent state preferably follows the state of system 200 illustrated in FIG. 2C. As appreciated from consideration of the appearance of screen 206 in FIG. 2D in comparison to that in FIG. 2C, balloon 242 has preferably undergone virtual motion in the progression from FIG. 2C to FIG. 2D, so as to move to a new position on screen 206 in FIG. 2D. Here, by way of example, butterfly 240 is no longer displayed and balloon 242 is seen to be reduced in size in FIG. 2D compared to FIG. 2C and to have moved in a temporal direction, here shown as a direction away from the center of screen 206. Such virtual motion of balloon 242 as viewable by eye 204 of a subject serves to create an impression that balloon 242 is now receding from the subject and thus promotes relaxation of accommodation by lens 246 of eye 204 tracking apparent, virtual motion of balloon 242. As seen in FIG. 2D, lens 246 becomes thinner and longer due to the relaxation of accommodation as a result of the perception by eye 204 of balloon 242 becoming further away from eye 204.

The perception by eye 204 of balloon 242 becoming more remote from the viewer is preferably enhanced by way of axial movement of screen 206 away from collimating lens 210, along a direction indicated by an arrow 254, such that screen 206 is located axially beyond the focal distance of collimating lens 210. Such movement of screen 206 preferably serves to enhance the perception of balloon 242 as receding from the subject and thus encourages relaxation of accommodation by eye 204.

It is appreciated that the virtual motion of balloon 242 on screen 206 is thus complemented by the physical motion of screen 206 so as to augment the apparent motion of balloon 242 away from eye 204 and thus more effectively relax accommodation by eye 204. It is understood, however, that the physical motion of screen 206 may alternatively be obviated and the perception of balloon 242 as receding from eye 204 induced solely by way of virtual motion of balloon 242 on screen 206.

Figure 2E:
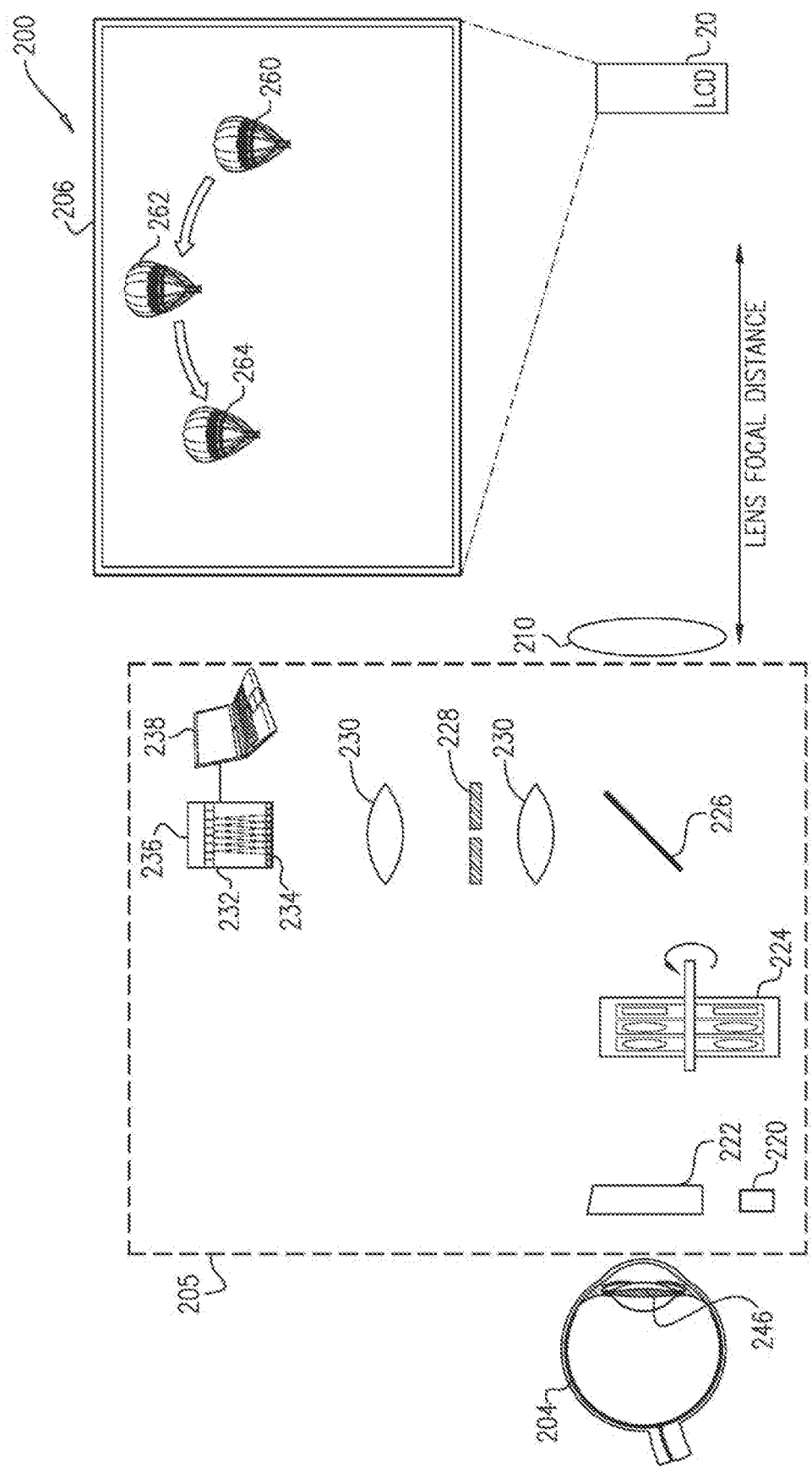

FIG. 2E shows a subsequent state of system 200, which subsequent state preferably follows the state of system 200 illustrated in FIG. 2D. As appreciated from consideration of the appearance of screen 206 in FIG. 2E in comparison to that in FIG. 2D, balloon 242 has preferably undergone virtual motion in the progression from FIG. 2D to FIG. 2E, so as to move to a new position on screen 206 in FIG. 2E. Here, by way of example, balloon 242 is seen to be non-static on screen 206 in FIG. 2E and to move, by way of example, from a first position 260 to a second position 262 and a third position 264. The motion of balloon 242 preferably serves to prolong tracking of balloon 242 by eye 204 of a subject, such that the subject becomes immersed in the virtual environment provided by screen 206 and thus genuinely feels and perceives balloon 242 as a distant object and relaxes accommodation accordingly. Such immersion in the virtual environment provided by screen 206 is significant, since in the case that the subject remains aware that the virtual reality object, such as balloon 242, is not truly distant but rather is simply being displayed as such, this awareness by the subject influences the extent of accommodation by eye 204 of the subject and prevents full relaxation of accommodation, thus interfering with subsequent objective and/or subjective visual test results.

Figure 2F:
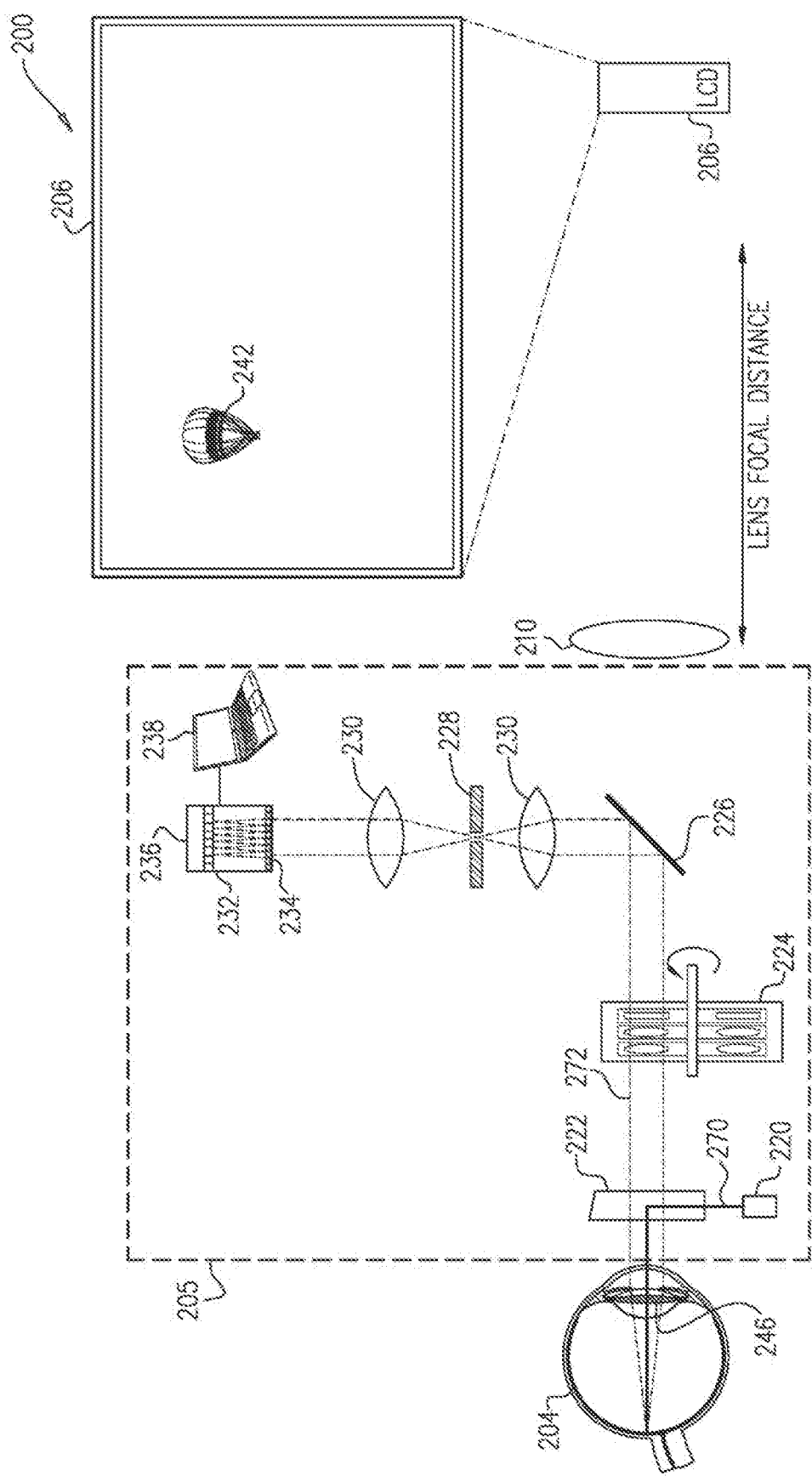

FIG. 2F shows a subsequent state of system 200, which subsequent state preferably follows the state of system 200 illustrated in FIG. 2E. As appreciated from consideration of the appearance of screen 206 in FIG. 2F in comparison to that in FIG. 2E, balloon 242 is preferably static in FIG. 2F rather than in motion as in FIG. 2E. Upon balloon 242 becoming static in FIG. 2F, objective wavefront analysis testing is preferably applied, wherein a beam of light 270 is preferably directed from laser 220 towards eye 204 via beam splitter 222 and a reflected beam of light 272 directed towards Shack-Hartmann sensor 232 through phoropter 224, additional beam splitter 226 and pin-hole and lens pair 228 and 230. Such objective wavefront analysis testing may also be termed auto-refraction and provides an objective measurement of refractive properties of eye 204. It is appreciated that the induced relaxation of accommodation by eye 204, achieved through the virtual motion of butterfly 240 and balloon 242 on screen 206 described hereinabove, serves to prevent or reduce errors in the auto-refraction measurement, which errors would otherwise be present due to accommodation by eye 204 during the performance of autorefractive testing. The results of such autorefraction are preferably similar in accuracy to refraction measurement results obtained by use of an open-field autorefractor.

Following the performance of autorefraction, as illustrated in FIG. 2F, the refractive properties of the eye are preferably approximately ascertained and the lenses of phoropter 224 set accordingly, preferably automatically by computer 238. Eye 204 must now be prepared for the performance of a subjective visual acuity test using phoropter 224. It is understood that since the subjective visual acuity test involves the viewing of a virtual reality test target on screen 206, accommodation by eye 204 is preferably deliberately induced and then relaxed before performance of the subjective test, in order to ensure that the awareness by the subject of being in a virtual reality testing set up does not lead to an accommodative response by the subject, thus interfering with the subjective test results.

It is appreciated that since eye 204 is in a deliberately relaxed non-accommodative state prior to the performance of the objective refraction measurement of FIG. 2F, the accommodative state of eye 204 may be assumed to remain unchanged and a subjective visual acuity test involving phoropter 224 performed immediately thereafter. However, in order to ensure greatest accuracy of testing by phoropter 224, the accommodation by eye 204 is preferably deliberately again induced and relaxed prior to the performance of a subjective visual test, as described hereinbelow with reference to FIGS. 2G-2I.

Figure 2G:
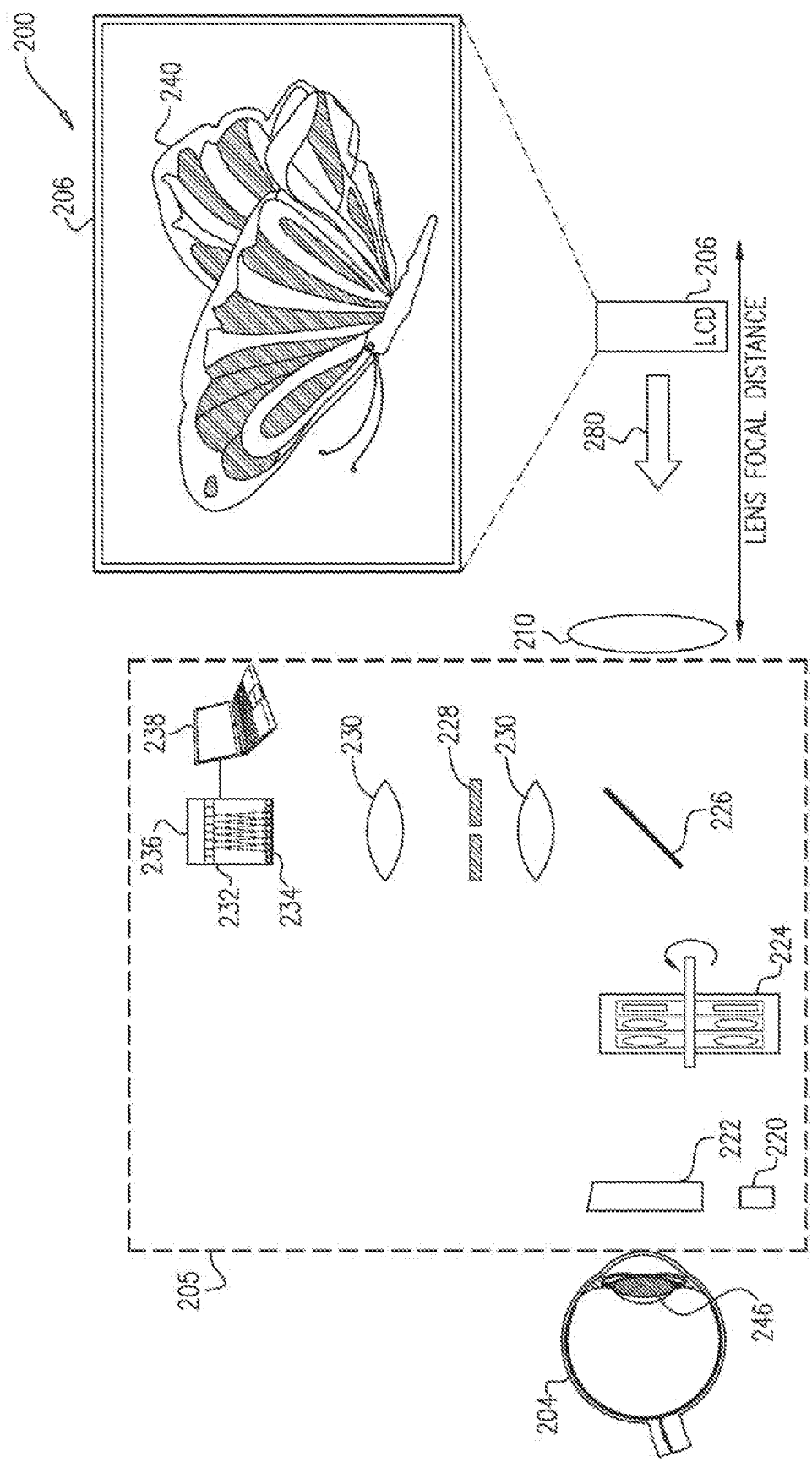

FIG. 2G shows a subsequent state of system 200, which subsequent state preferably follows the state of system 200 illustrated in FIG. 2F. As appreciated from consideration of the appearance of screen 206 in FIG. 2G in comparison to that in FIG. 2F, butterfly 240 is seen to be shown in an enlarged form in FIG. 2G and to have moved in a nasal direction, here shown as a direction towards the center of screen 206. Such virtual motion of butterfly 240 as viewable by eye 204 of a subject serves to create an impression that butterfly 240 is approaching the subject and thus induces accommodation by eye 204 viewing butterfly 240. As seen in FIG. 2G, lens 246 of eye 204 is shown to become thicker and shorter due to the induction of accommodation as a result of the perception by eye 204 of butterfly 240 becoming closer thereto.

The perception by eye 204 of butterfly 240 approaching the subject is preferably enhanced by way of axial movement of screen 206 towards collimating lens 210, along a direction indicated by an arrow 280, such that screen 206 is located closer to collimating lens 210 than the focal distance thereof. Such movement of screen 206 preferably serves to enhance the perception of butterfly 240 as approaching the subject and thus further encourages accommodation by eye 204. It is appreciated that the virtual motion of butterfly 240 on screen 206 is thus complemented by the physical motion of screen 206 so as to augment the apparent motion of butterfly 240 towards eye 204 and thus more effectively induce accommodation by eye 204. It is understood, however, that the physical motion of screen 206 may alternatively be obviated and the perception of butterfly 240 approaching eye 204 induced solely by way of virtual motion of butterfly 240 on screen 206.

Figure 2H:
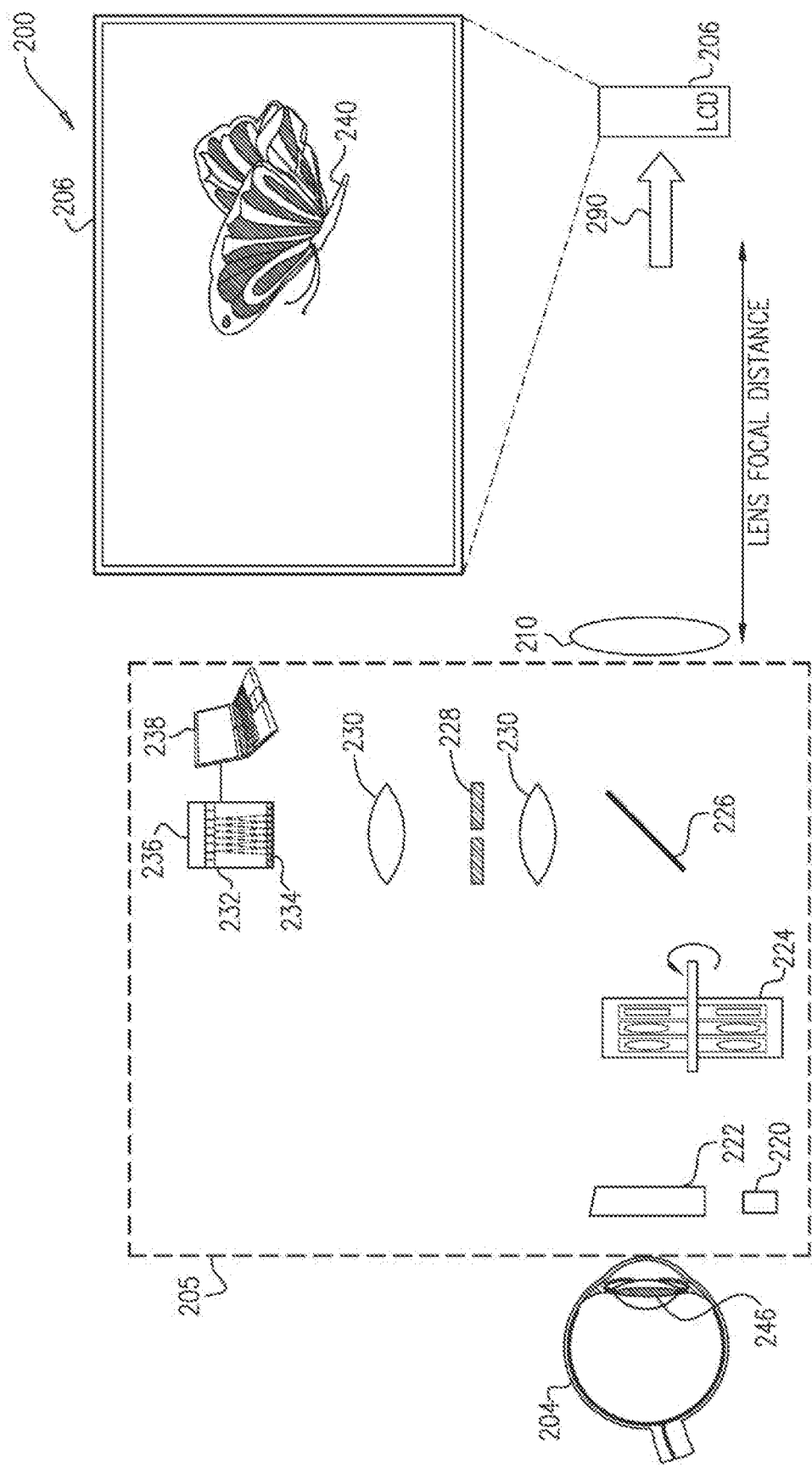
Figure 21:
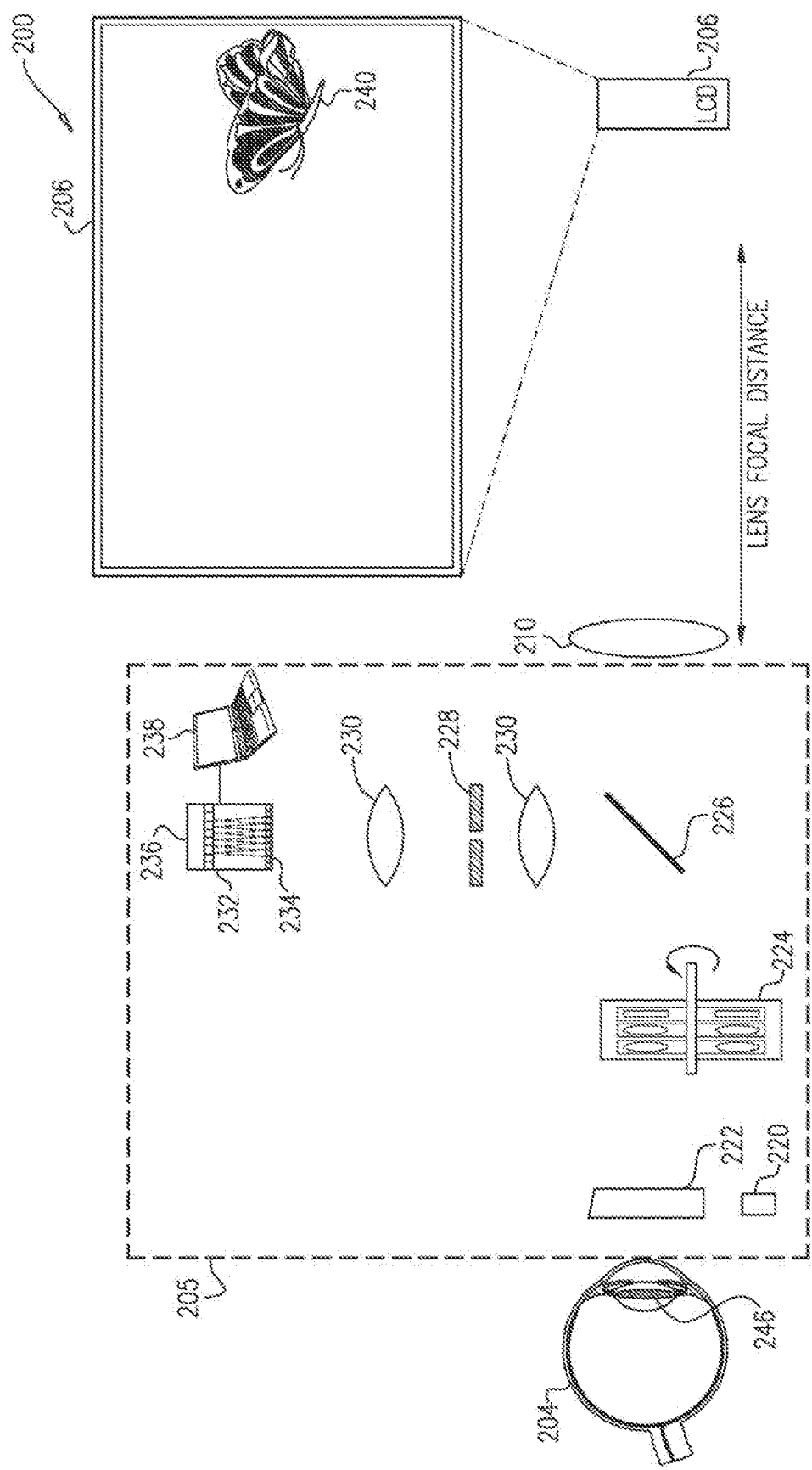

FIG. 2H shows a further subsequent state of system 200, which subsequent state preferably follows the state of system 200 illustrated in FIG. 2G. As appreciated from consideration of the appearance of screen 206 in FIG. 2H in comparison to that in FIG. 2G, butterfly 240 has undergone yet further virtual motion in the progression from FIG. 2G to FIG. 2H, so as to assume a new position on screen 206 in FIG. 2H. Here, by way of example, butterfly 240 is seen to be reduced in size in FIG. 2H compared to FIG. 2G and to have moved in a temporal direction, here shown as corresponding to a direction away from the center of screen 206. Such virtual motion of butterfly 240 as viewable by eye 204 of a subject serves to create an impression that butterfly 240 is now receding from the subject and thus initiates relaxation of accommodation by lens 246 of eye 204 viewing butterfly 240. As seen in FIG. 2H, lens 246 becomes thinner and longer due to the relaxation of accommodation as a result of the perception by eye 204 of butterfly 240 becoming further away from eye 204.

The perception by eye 204 of butterfly 240 becoming more remote from the viewer is preferably enhanced by way of axial movement of screen 206 away from collimating lens 210, along a direction indicated by an arrow 290, such that screen 206 is located axially beyond the focal distance of collimating lens 210. Such movement of screen 206 preferably serves to enhance the perception of butterfly 240 as receding from the subject and thus encourages relaxation of accommodation by eye 204. Butterfly 240 would typically be perceived as blurred by eye 204 in the arrangement illustrated in FIG. 2H, due to the location of screen 206 at a point beyond the focal distance of collimating lens 210.

It is appreciated that the virtual motion of butterfly 240 on screen 206 is thus complemented by the physical motion of screen 206 so as to augment the apparent motion of butterfly 240 away from eye 204 and thus more effectively relax accommodation by eye 204. It is understood, however, that the physical motion of screen 206 may alternatively be obviated and the perception of butterfly 240 as receding from eye 204 induced solely by way of virtual motion of butterfly 240 on screen 206.

In order to further promote release of accommodation following the induction of accommodation in FIG. 2G, the lens arrangement of phoropter 224 may be reset by adding a positive dioptric power of, for example, +1D in order to create a fogging effect and further promote relaxation of accommodation by eye 204, prior to the display to eye 204 of display screen 206 of the type shown in FIG. 2H.

FIG. 2I shows a further subsequent state of system 200, which subsequent state preferably follows the state of system 200 illustrated in FIG. 2H. As appreciated from consideration of the appearance of screen 206 in FIG. 2I in comparison to that in FIG. 2H, butterfly 240 has undergone yet further virtual motion in the progression from FIG. 2H to FIG. 2I, so as to assume a new position on screen 206 in FIG. 2I. Here, by way of example, butterfly 240 is seen to be further reduced in size in FIG. 2I compared to FIG. 2H and to have further moved in a temporal direction, here shown as away from the center of screen 206. Such virtual motion of butterfly 240 as viewable by eye 204 of a subject serves to create an impression that butterfly 240 is further receding from the subject and thus further promotes relaxation of accommodation by lens 246 of eye 204 viewing butterfly 240.

It is understood that the virtual motion of butterfly 240 on screen 206, so as to induce and subsequently relax accommodation by eye 204 of a subject viewing screen 206, is illustrated in discrete steps in FIGS. 2G-2I for ease of representation only and that in actuality, the progression of virtual motion of butterfly 240 is preferably, although not necessarily, continuous and may involve the display of additional or alternative display screens than those illustrated in FIGS. 2G-2I.

At the point at which butterfly 240 has recessed to a predetermined distance as perceived by eye 204, such as 6 m, eye 204 is preferably in a fully relaxed non-accommodative state and a Snellen chart 294, or other equivalent visual target is preferably displaced to eye 204 on screen 206, as seen in FIG. 2J. Screen 206 is preferably located at the focal point of lens 210, movement of screen 206 in a direction towards this position being indicated by an arrow 296, and Snellen chart 294 is preferably displayed in the direct line of sight of eye 204 through beam splitter 226 and collimating lens 210. A standard subjective visual acuity test may then be performed by an operator of phoropter 224 on the eye 204 of a subject, as the subject views the virtual reality Snellen chart 294. It is understood that in the case that fogging was previously applied to the lens settings of phoropter 224 in order to aid release of accommodation, as described hereinabove, the added dioptric power is preferably subtracted from the test results during the visual acuity testing.

It is appreciated that the subjective visual acuity test applied by system 200 is thus preferably performed using a virtual reality visual target, such as Snellen chart 294, rather than a truly distant visual target as is conventionally the case. Such a conventional truly distant visual target, typically separated from the subject under test by a distance of 6 m, is impractical in many testing set-ups involving limited physical space. In the present invention, a highly compact virtual reality testing system is provided, in which the visual target may be extremely closely physically located with respect to the subject, for example at a distance of only 350 mm, but is perceived by the subject, who is immersed in the virtual reality scene displayed on screen 206, as being far away. Additionally, the physical distance between the display screen 206 and eye 204 may be even further reduced by the use of folding mirrors along the optical path therebetween.

Awareness by a viewer that a virtual reality target is indeed in close physical proximity, despite the appearance thereof, tends to lead to an accommodative response by the viewer, due to the psychological influence of the knowledge that the virtual reality object is physically near thereto. In the present invention, this automatic accommodative response by a subject viewing an apparently distant virtual reality target is advantageously overcome, by way of deliberate induction and relaxation of accommodation by the eye of the subject prior to performance of one or both of the objective and subjective visual tests. It is appreciated that in the absence of such deliberate induction and relaxation of accommodation, created by virtual reality motion of a virtual reality object on a virtual reality display screen in preferred embodiments of the present invention, the accommodative response of a viewer viewing the virtual reality display screen would lead to errors in both the objective and subjective visual tests.

It is appreciated that although the series of screens displayed in FIGS. 2A-2I are shown in relation to a single eye 204, this is for the purpose of simplicity of presentation only, and such screens are preferably displayed to both eyes of a viewer, preferably on individual respective screens, in order to immerse the viewer in a virtual reality environment. Similar or particularly preferably identical virtual reality objects, such as those illustrated in FIGS. 2A-2I, are preferably displayed to a subject on two individual display screens respectively aligned with each eye of the subject, at such a position on the individual screens such that the two eyes of the subject cooperate to merge the virtual reality objects on the two screens into a single perceived object.

Binocular display may be carried out using a binocular display system, as further detailed hereinbelow with reference to FIGS. 4A and 4B. However, during performance of a subjective visual acuity test, as described with reference to FIG. 2J, subjective testing is preferably performed individually, respectively for each eye of a viewer in a monocular fashion by displaying a single screen 206 to only a single respective eye of the viewer, following which binocular subjective testing may also be performed.

It is also appreciated that the particular appearances and types of motion of virtual reality objects, including butterfly 240 and balloon 242, shown in FIGS. 2A-2J are exemplary only and that embodiments of the present invention may include the display of any type of 2D or 3D virtual reality object undergoing virtual motion, which virtual motion as viewable by a subject is operative for inducing and relaxing accommodation by at least one eye of the subject. Particularly, preferred embodiments of the present invention include the display on a virtual reality display device of virtual motion of at least one virtual reality object leading to the perception by the viewer of the virtual reality object approaching and/or receding from the viewer, as well as types of motion serving to immerse the viewer in the virtual reality environment presented by the virtual reality display device.

Figure 3A:
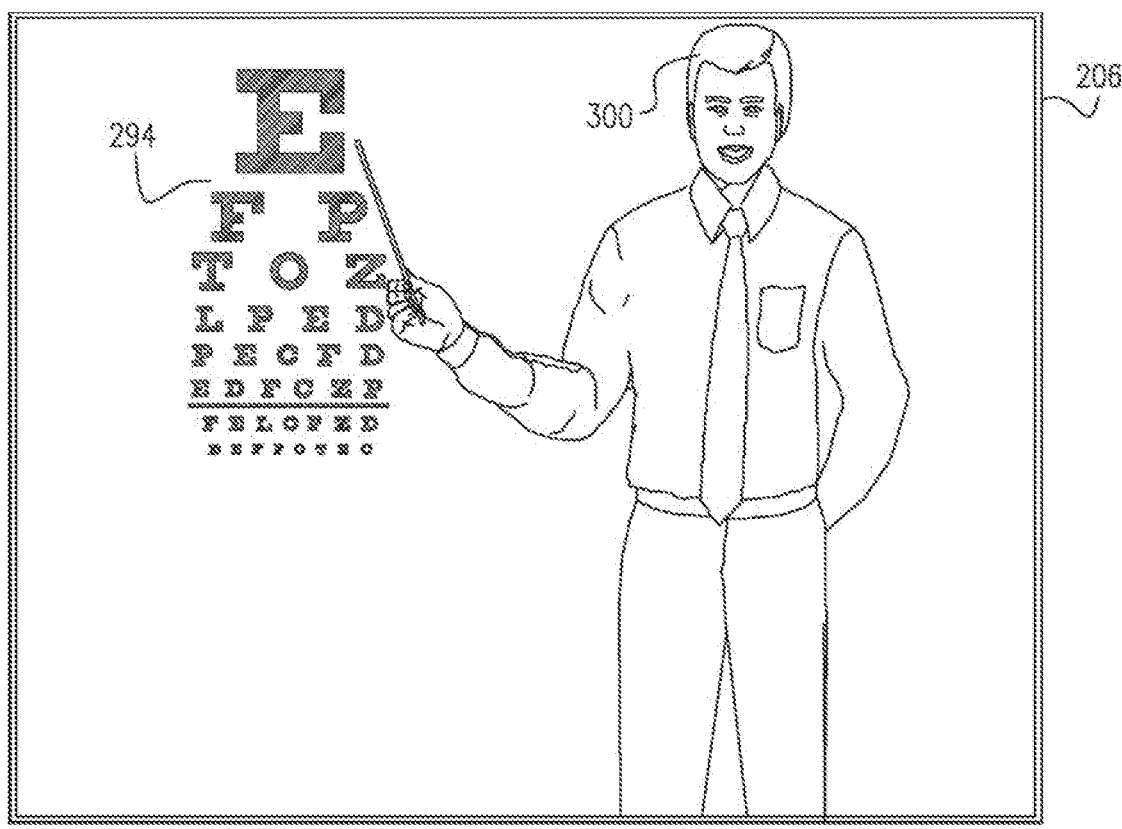
FIGS. 3A and 3B are simplified schematic illustrations of additional virtual reality display screens useful in a virtual reality display system of any of the types illustrated in FIGS. 1A-2J.

By way of example, as illustrated in FIG. 3A, Snellen chart 294 may be displayed on screen 206 in relation to an individual 300, wherein perception of the distance of chart 294 is changed by way of changing of the apparent size of individual 300 in relation to chart 294. Additionally, the inclusion of individual 300 pointing out letters to be read on Snellen chart 294 preferably serves to further immerse the subject in the virtual testing environment created by screen 206, by making the testing set-up displayed on screen 206 appear more natural.

Figure 3B:
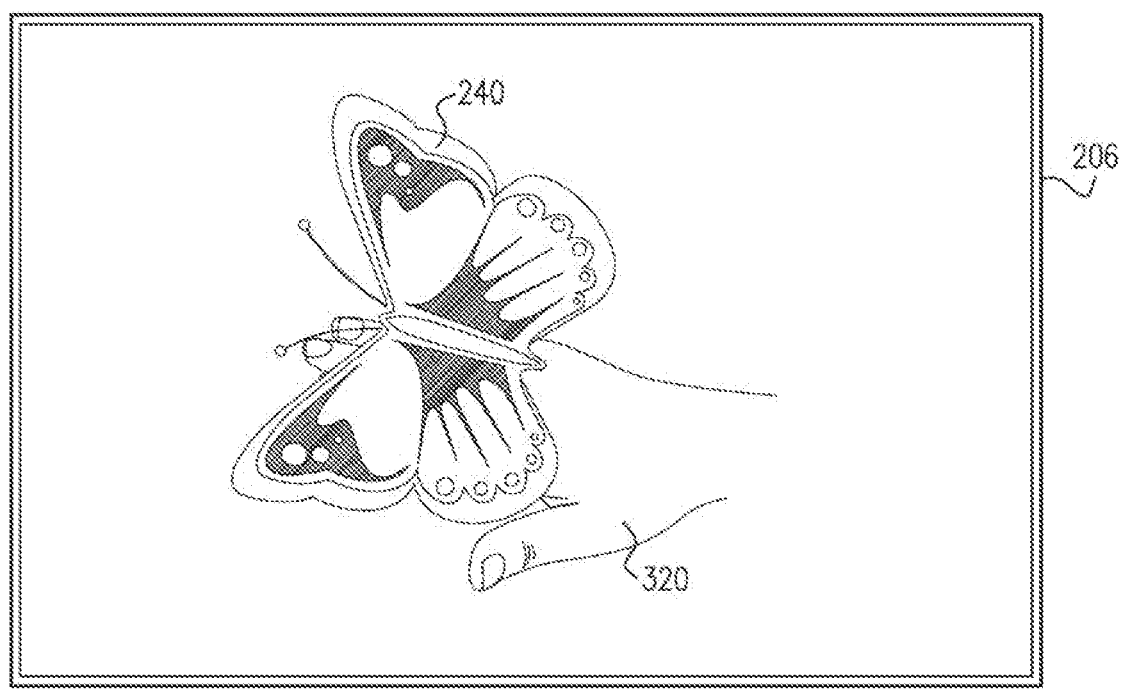

Further by way of example, as illustrated in FIG. 3B, one virtual reality object such as butterfly 240 may be shown in relation to another virtual reality object, such as a hand 320, in order to further promote the perception of butterfly 240 being in close proximity to the subject. Changes in the relative size, position and clarity of one or both of the virtual reality objects preferably leads to changes in perception and hence accommodation by the viewer. Additionally or alternatively, the convergence angle of the virtual reality display screen, such as display screen 206, may be changed so as to be in keeping with the convergence associated with near and far field viewing. It is appreciated that although the tilting of the optical alignment system for the purposes of changing the convergence angle is not shown in relation to system 200, such tilting may be performed in a nasal direction in order to enhance the perception by the subject of near viewing.

It is appreciated that although a preferred embodiment of the present invention illustrated in FIGS. 2A-2J is useful for performing objective and subjective refraction and visual acuity tests, the present invention is not limited to implementation within a visual acuity testing device of the type shown. Other possible applications of the virtual reality display system of the present invention include measurement of Accommodative Convergence/Accommodation (AC/A) and Convergence Accommodation/Convergence (CA/C) ratios, color vision tests, contrast sensitivity tests, night vision testing, monocular amplitude of accommodation testing, pupillary response testing, strabismus screening, 3D vision tests and visual acuity in motion tests.

In measurement of the AC/A ratio, the ratio of the angle over which the eyes converge in response to a change in accommodation is measured. In performance of such a test using the virtual reality display system of the present invention, eye movement in the nasal and/or temporal direction may be measured as the virtual reality display screen and/or virtual reality objects displayed thereon are moved from a far to near focal position. The eye position may be monitored by a camera, in order to measure the movement of the pupil of the eye during the accommodation process.

In measurement of the CA/C ratio, convergence accommodation may be measured by moving a virtual reality target displayed on a virtual reality screen in a nasal direction whilst keeping the screen at a fixed position, at the focus of the collimating lens. The refraction of both eyes may then be measured by an objective refractive measurement system, such as by way of Shack-Hartmann sensor 232. Maintenance of the display screen at a fixed, far, position allows separation between the near accommodative stimulus accommodation arising from the eyes focusing on the virtual reality target and convergence accommodation due to the target movement in a nasal direction. The convergence accommodation may be measured by the Shack-Hartmann sensor 232 and the CA/C ratio calculated correspondingly.

In performance of a color vision test, suitably colored images as are well known in the art, such as a series of Ishihara PIC test plates, may be displayed to a subject on two virtual reality display screens respectively aligned with each eye of the subject, and the color vision of the subject thereby assessed.

In performance of a contrast sensitivity test, a suitable contrast sensitivity chart, such as a Pelli-Robson letter contrast sensitivity chart, may be displayed to a subject on two virtual reality display screens respectively aligned with each eye of the subject, and the contrast of legible and illegible letters noted.

In performance of night vision testing, a visual acuity test such as described hereinabove with reference to FIGS. 2A-2J may be performed under low lighting conditions such that the pupil of the eye is dilated and a wavefront sensor, such as Shack-Hartmann sensor 232, may analyze data available from the entire pupil area. Individual analyses may be carried out for different pupil areas, in order to calculate both day and night vision. The objective analyses may be verified by subjective testing, such as by using phoropter 224.

In performance of monocular amplitude of accommodation testing using the system of the present invention, a stimulus in the form of a virtual reality target may be displayed to a subject and the refraction of each eye of the subject measured as the stimulus is moved from infinity towards the eye. A display screen is preferably initially placed at the focus of the collimating lens, such that a virtual reality target displayed thereon is at optical infinity with respect to the eye of the subject, and the refraction of the eye then measured, for example by using Shack-Hartmann sensor 232. The display screen is then preferably incrementally moved in a direction towards the eye and the refraction of the eye measured for each screen position. Such displacement and measurement is preferably continued until no further change in wavefront measurement is recorded, indicating that maximum accommodation has been reached. This testing is preferably carried out in a monocular fashion, for each eye individually.

In performance of pupillary response testing using the system of the present invention, illumination of the display screens may be varied and a camera used to measure the corresponding pupil size. The illumination levels of the screens may be incrementally increased or decreased and the time response of the pupil at each illumination level recorded. This testing is preferably carried out separately for each eye of a subject, allowing pupillary measurement to be made at each illumination level for both the illuminated and fellow pupil.

In performance of strabismus screening using the system of the present invention, the position of a virtual reality object on a display screen may be varied and the corresponding pupil gaze direction monitored by a camera, in order to evaluate the ability of the eyes of a subject to correctly fixate on a target. Preferably, each eye is initially separately tested by displaying a blank screen to a first eye not presently being tested and a virtual reality object on a second screen to a second eye, the direction of gaze of the second eye being measured by a camera. The testing situation is then reversed, with the direction of gaze of the first eye observing a virtual reality target on a first screen being tested and a blank screen being displayed to the second eye. Both eyes may be readily observed during the transition period between the eye being presented with an image and being presented with a blank screen, which transition period observation is typically more difficult to achieve in conventional Strabismus cover testing protocols.

In performance of 3D vision tests using the system of the present invention, different images may be displayed on two display screens respectively aligned with each eye of a viewer. For particular viewing angles, depending on the binocular visual ability of the viewer, parts of the images as seen both by eyes with appear to be three dimensional and will protrude from the rest of the image which will appear to be two dimensional. The viewer may report to an examiner on those parts of the image perceived to be three dimensional, whereby the three dimensional visual capabilities of the viewer may be evaluated.

In performance of visual acuity in motion testing using the system of the present invention, the position of a visual target such as a test chart may be moved on one or both display screens with constant or changing frequency and velocity, during testing for visual acuity. Such testing may be used to detect vestibular deficits including vertigo, dizziness and imbalance.

In one preferred embodiment of the present invention, system 200 may be operative for use in performing prismatic measurements, following the deliberate induction and release of accommodation of the eye of the subject as described hereinabove. A virtual reality object, such as butterfly 240, balloon 242 or Snellen chart 294, may be displayed to a subject being tested for prismatic aberrations including phoria and tropia. The virtual reality object may be located at a variety of positions on display screen 206 with respect to eye 204 of the subject, which variety of positions preferably corresponds to a variety of deflection angles of the image from the center of the non-aberrated line of sight of the subject. Relocation of the virtual reality object on the display screen at various locations with respect to the center of the screen, as viewable by the subject, thus causes the subject to view the virtual reality object at a variety of deflection angles, allowing testing for the presence and extent of prismatic aberrations of the subject. It is appreciated that the display of the virtual reality object on the display screen at different positions corresponding to different angles of deflection, obviates the need for use of prismatic lenses for deflecting light beams and thus deflecting the apparent location of the object being viewed by the user. Phoropter 224 therefore needs not include prismatic lenses for the testing and correction of prismatic aberrations, thus simplifying the structure of phoropter 224 and the performance of prismatic testing by system 200.

In another preferred embodiment of the present invention, system 200 may be operative for use as a field perimeter device, for testing the field of view of a subject, following the deliberate induction and release of accommodation of the eye of the subject as described hereinabove. In operation of system 200 as a field perimeter device, virtual reality objects, such as butterfly 240 and balloon 242, may be displayed to a subject at a variety of positions on screen 206, the subject being asked to react upon seeing the virtual reality object. The angular field of view of the subject may then be assessed based on the range of positions of the virtual reality objects to which the subject reacts. Such field of view measurements may be particularly useful for the detection and monitoring of conditions leading to progressive narrowing of the field of view of a subject, such as glaucoma.

It is appreciated that although systems 100 and 200 are shown as monocular systems in relation to a single eye, 104 or 204, the system of preferred embodiments of the present invention may be constructed and operative as a binocular system, for sequentially or simultaneously examining both eyes of a subject. A simplified illustration of a binocular system in respective first and second states thereof, constructed and operative in accordance with preferred embodiments of the present invention, is illustrated in FIGS. 4A and 4B.

Figure 4A:
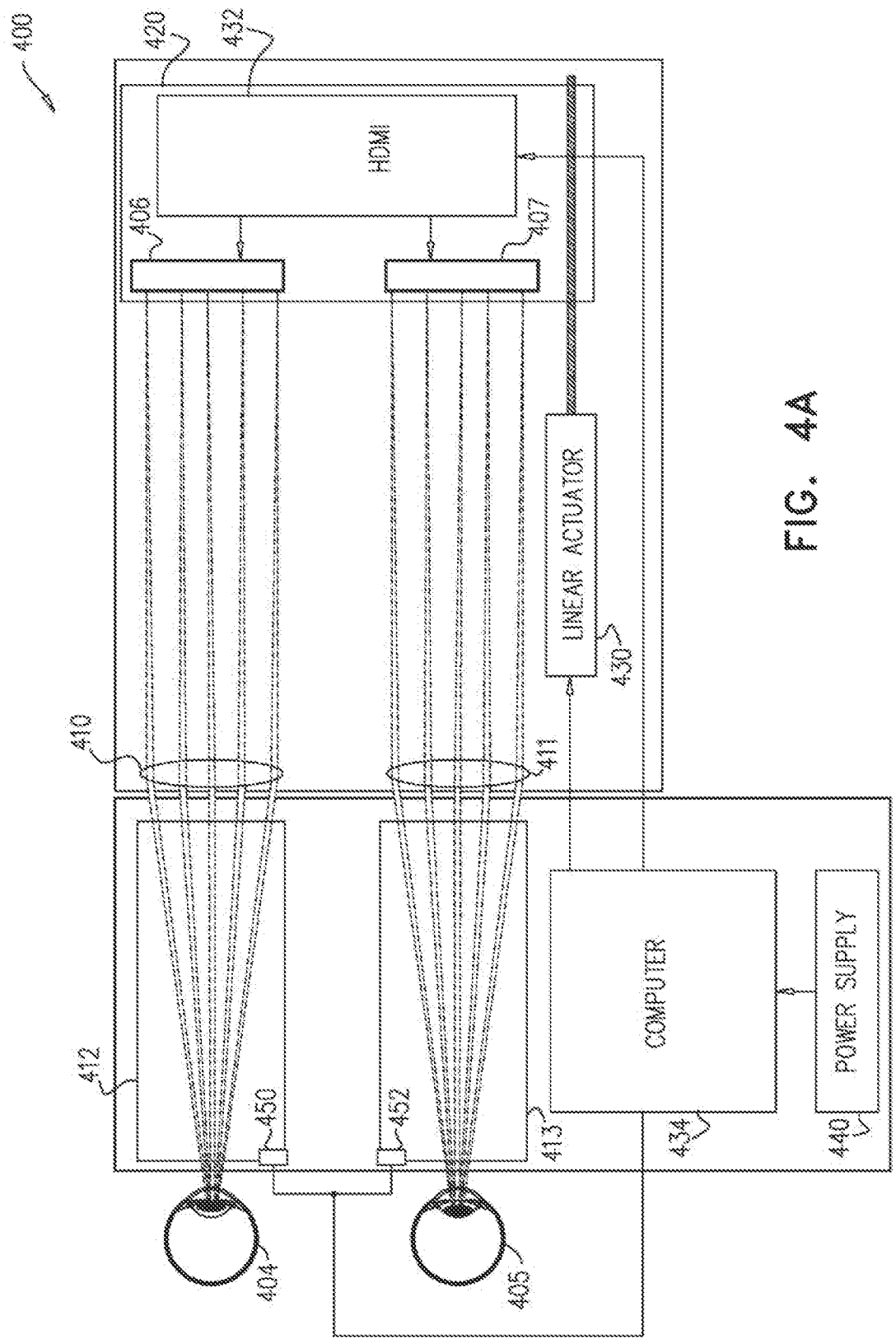
FIGS. 4A and 4B are simplified schematic, partially block diagram illustrations of an optical examination device including a virtual reality display system in respective first and second states thereof, constructed and operative in accordance with yet another preferred embodiment of the present invention.
Figure 4B:
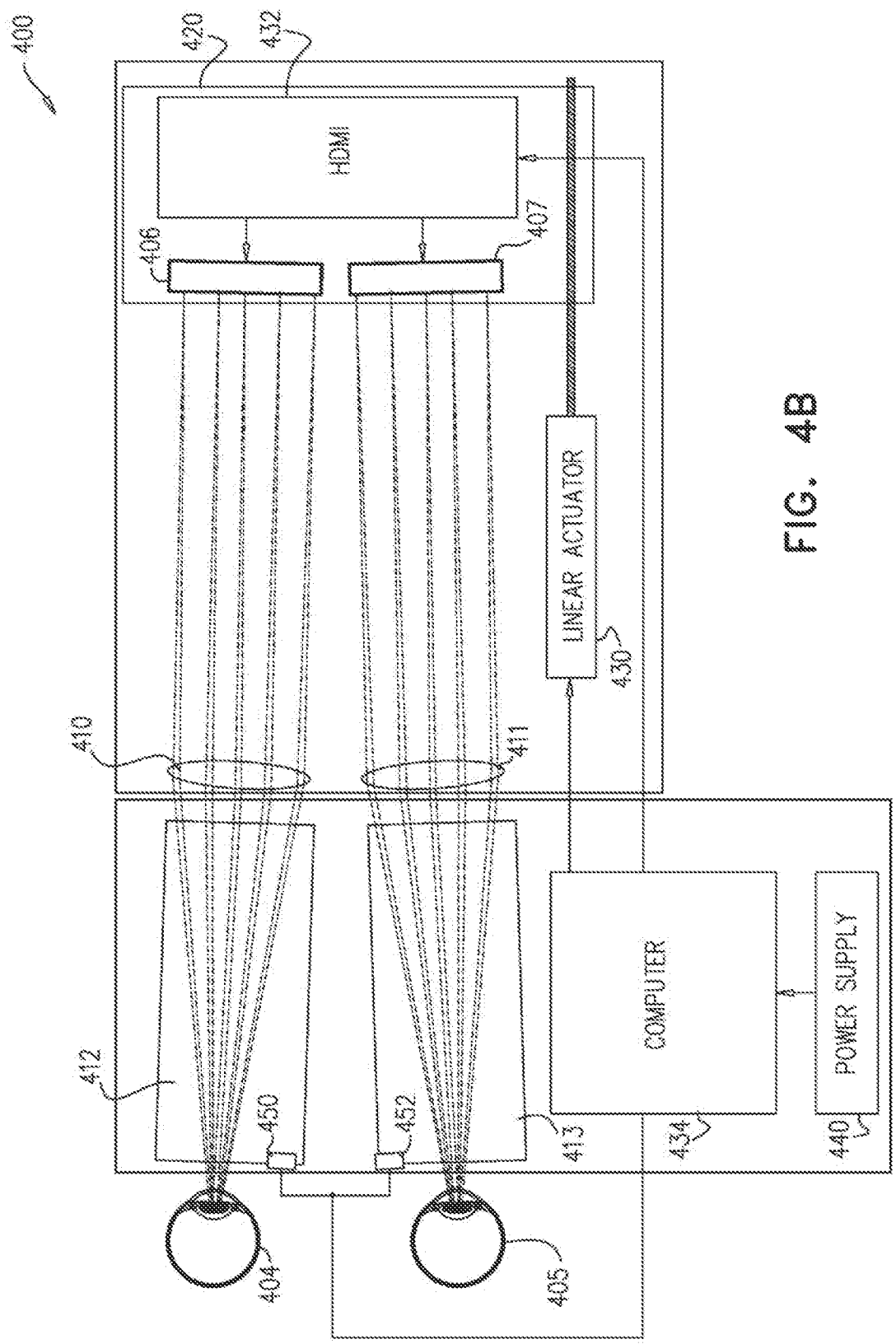

As seen in FIGS. 4A and 4B, there is provided an optical examination device 400 for binocular and/or monocular testing of a first eye 404 and a second eye 405 of a subject. First eye 404 is preferably optically aligned with a first virtual reality display device, here embodied by way of example as a first virtual reality display screen 406. Second eye 405 is preferably optically aligned with a second virtual reality display device, here embodied by way of example as a second virtual reality display screen 407. Light emanating from first display screen 406 is preferably collimated by way of a first collimating element, here embodied as a first collimating lens 410. Light emanating from second display screen 407 is preferably collimated by way of a second collimating element, here embodied as a second collimating lens 411. First eye 404 is preferably aligned with a first optical alignment subsystem 412 and second eye 405 is preferably aligned with a second optical alignment subsystem 413.

In accordance with preferred embodiments of the present invention, first and second optical alignment subsystems 412 and 413 may respectively comprise elements of individual, separate first and second optical testing subsystems, such as subsystem 205, and particularly elements of first and second phoropter devices thereof, such as phoropter device 224, for optically aligning and directing light between first and second eye 404 and 405 and first and second display screens 406 and 407, respectively.

Display screens 406 and 407 are preferably mounted on a stage 420, linear motion of which stage 420 in a direction axially towards or away from eyes 404 and 405 is preferably controlled by a linear actuator 430. Display screens 406 and 407 may be coupled to a transmitting interface such as an HDMI interface 432 connected to a computing device 434. Computing device 434 is preferably additionally connected to linear actuator 430 in order to control the motion thereof. Computing device 434 is preferably powered by a power supply 440.

Device 400 may optionally include at least one tilting motor, here embodied, by way of example, as a first tilting motor 450 preferably coupled to first optical alignment system 412 and a second tilting motor 452 preferably coupled to second optical alignment system 413. As seen in FIG. 4A, illustrating a first state of system 400, elements corresponding to each of first and second eyes 404 and 405, including optical alignment elements 412 and 413, collimating lenses 410 and 411 and screens 406 and 407, may be arranged in a mutually parallel arrangement, suitable for many optical examination procedures. In this case, tilting motors 450 and 452 are not operational and optical alignment elements 412 and 413 and screens 406 and 407 are axially aligned.

As seen in FIG. 4B, illustrating a second state of system 400, in certain testing or accommodation induction situations, it may be advantageous to tilt the optical elements corresponding to each of eyes 404 and 405. In this case, tilting motors 450 and 452 may be operative to tilt the optical elements corresponding to each of eyes 404 and 405, in order to change the convergence angles of screens 406 and 407 as respectively viewed by eyes 404 and 405, thereby better emulating convergence. Such a tilted arrangement may be used for testing in an accommodative state, or in cases where screens 406 and 407 are moved very close to eyes 404 and 405. It is appreciated that the tilting angle illustrated in FIG. 4B is illustrative only, and that a greater or smaller tilting angle may be employed, depending on the system architecture as well as the desired screen convergence.

As noted hereinabove, system 200, including optical testing subsystem 205, may preferably be constructed in accordance with the architecture of system 400, wherein the system may be initially operated in a binocular fashion, with both of screens 406 and 407 being activated in order to immerse the subject in the virtual reality environment, and monocular visual acuity testing subsequently performed by sequential activation of screens 406 and 407. During operation of system 400 in a binocular fashion, a similar or identical virtual reality object is preferably simultaneously displayed on both of screens 406 and 407, at such a position on the individual screens 406 and 407 that eyes 404 and 405 preferably cooperate to merge the two virtual reality objects into a single perceived 2D or 3D object.

Figure 5:
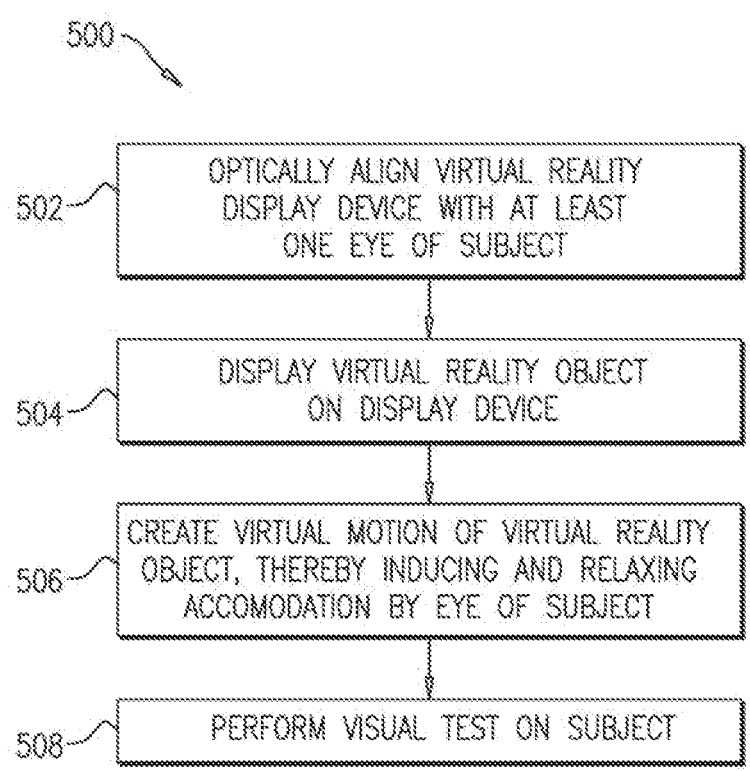
FIG. 5 is a simplified flow chart illustrating steps in performance of an ocular examination employing a virtual reality display, constructed and operative in accordance with a preferred embodiment of the present invention.

Reference is now made to FIG. 5, which is a simplified flow chart illustrating steps in performance of an ocular examination employing a virtual reality display, constructed and operative in accordance with a preferred embodiment of the present invention.

As seen in FIG. 5, an examination process 500 may begin at a first step 502 in which a virtual reality display device, such as device 106, 206, 406 or 407, is optically aligned with at least one eye of a subject under test. Following alignment of the display device with the eye of the subject, at least one virtual reality object is preferably displayed to the subject on the display device, as seen at a second step 504. As seen at a third step 506, virtual motion of the virtual reality object is then created, in order to induce and relax accommodation by the eye of the subject viewing the virtual reality object. Such virtual motion may include at least one of receding motion, advancing motion, change in at least one of size and position of the virtual object displayed on the virtual reality display device, change in at least one of size and position of the virtual object with respect to another virtual reality object displayed on the virtual reality display device, blurring of the virtual reality object as perceivable by the subject, improving clarity of the virtual reality object as perceivable by the subject and changing the convergence angle of the virtual reality display device.

As seen at a fourth step 508, following the induction and relaxation of accommodation by the subject, a visual test may be performed upon the subject. The visual test performed at fourth step 508 may be an objective visual test, subjective visual test or both. It is appreciated that performance of the visual test on the subject following relaxation of accommodation by the subject, as achieved at third step 506, minimizes or obviates errors in visual testing resulting from an accommodative response by the subject during testing.

It is appreciated that first-fourth steps 502-508 in process 500 are set forth in a highly general manner and may be supplemented by additional or alternative steps, depending on the particular application involved. Furthermore, it is appreciated that the steps are not necessarily performed in the order listed. By way of example, first step 502 may be preceded by second step 504 or may be performed simultaneously therewith. Further by way of example, first-third steps 502-506 may be carried out prior to the performance of an objective visual test at fourth step 508, following which objective test first-third steps 502-506 may then be repeated, prior to the performance of a subjective visual test.

It will also be appreciated by persons skilled in the art that the present invention is not limited by what has been particularly claimed hereinbelow. Rather, the scope of the invention includes various combinations and subcombinations of the features described hereinabove as well as modifications and variations thereof as would occur to persons skilled in the art upon reading the foregoing description with reference to the drawings and which are not in the prior art.

The invention claimed is:

1. A virtual reality display system comprising:
   first and second optical alignment subsystems respectively optically aligned with a first eye and a second eye of a subject; and
   first and second tiltable display devices respectively optically aligned with said first and second optical alignment subsystems for providing a virtual reality environment to said subject by simultaneously displaying to said subject respective first and second objects, perceivable by said subject as being a three-dimensional virtual reality object, undergoing motion, said motion of said virtual reality object, as viewable by said subject, being operative to induce and relax accommodation by said eyes of said subject;
   each of said first and second tiltable display devices being tilted in relation to one another and in relation to said subject during said motion of said virtual reality object for induction of said accommodation,
   each of said first and second tiltable display devices being moved linearly towards said subject, when being tilted, during said motion of said virtual reality object for said induction of accommodation.

2. A system according to claim 1, wherein said motion of said three-dimensional virtual reality object comprises at least one of receding motion, advancing motion, change in at least one of a size and position of said three-dimensional virtual reality object, blurring of said three-dimensional virtual reality object as perceivable by said subject and improving clarity of said three-dimensional virtual reality object as perceivable by said subject.

3. A system according to claim 1, and also comprising first and second light collimating elements respectively interfacing said first and second tiltable display devices and said first and second optical alignment subsystems for collimating light emanating from said first and second tiltable display devices.

4. An ocular examination system comprising:
   first and second ocular testing subsystems respectively comprising first and second optical alignment subsystems respectively optically aligned with a first eye and a second eye of a subject; and
   first and second tiltable display devices respectively optically aligned with said first and second optical alignment subsystems for providing a virtual reality environment to said subject by simultaneously displaying to said subject respective first and second objects perceivable by said subject as being a three-dimensional virtual reality object, undergoing motion, said motion of said virtual reality object, as viewable by said subject, being operative to induce and relax accommodation by said eyes of said subject,
   said first and second tiltable display devices being tilted in relation to one another and in relation to said subject during said motion of said virtual reality object for induction of said accommodation,
   each of said first and second tiltable display devices being moved linearly towards said subject, when being tilted, during said motion of said virtual reality object for said induction of accommodation, wherein
   said first and second ocular testing subsystems perform a visual test on said subject following said motion for relaxation of accommodation.

5. A system according to claim 4, wherein said ocular testing subsystem comprises at least one of an objective testing subsystem and a subjective testing subsystem.

6. A system according to claim 5, wherein said visual test comprises at least one of a prismatic measurement, a field perimeter measurement, a three-dimensional vision test, a color vision test, a contrast sensitivity test, a vision acuity in motion test, a night vision test, a monocular amplitude of accommodation test, a CA/C and AC/A ratio test, a strabismus test, and a pupillary response test.

7. A system according to claim 5, wherein said ocular testing subsystem comprises a combined phoropter and auto-refraction device.

8. A system according to claim 7, wherein said ocular testing subsystem comprises a visual acuity testing subsystem and said three-dimensional virtual reality object comprises a virtual reality visual acuity testing target displayed on said tiltable display devices.

9. A system according to claim 8, wherein said virtual reality visual acuity testing target comprises a Snellen chart.

10. A method for performing an ocular examination on a subject comprising:

optically aligning first and second tiltable display devices with a first eye and a second eye respectively of a subject;

displaying to said subject, simultaneously on said first and second tiltable display devices, respective first and second objects, perceivable by said subject as being a three-dimensional virtual reality object;

creating motion of said three-dimensional virtual reality object as viewable by said subject, wherein said motion, as viewable by said subject, is operative to induce and relax accommodation by said eyes of said subject;

tilting said first and second tiltable display devices in relation to one another and in relation to said subject during said motion of said virtual reality object for induction of said accommodation, moving each of said first and second tiltable display devices linearly towards said subject, when being tilted, during said motion of said virtual reality object for said induction of accommodation, and performing at least one visual test on said subject following said motion for relaxation of accommodation.

11. A method according to claim 10, wherein said at least one visual test comprises at least one of an objective visual test and a subjective visual test.

12. A method according to claim 11, wherein said at least one visual test comprises at least one of a prismatic measurement, a field perimeter measurement, a three-dimensional vision test, a color vision test, a contrast sensitivity test, a vision acuity in motion test, a night vision test, a monocular amplitude of accommodation test, a CA/C and AC/A ratio test, a strabismus test, and a pupillary response test.

13. A method according to claim 10, wherein said at least one visual test comprises a combined subjective phoropter test and object wavefront analysis test.

14. A method according to claim 13, wherein said at least one visual test comprises a visual acuity test and said three-dimensional virtual reality object comprises a virtual reality visual acuity testing target displayed on said tiltable display devices.

15. A method according to claim 14, wherein said virtual reality visual acuity testing target comprises a Snellen chart.

16. A method according to claim 10, wherein said motion of said three-dimensional virtual reality object comprises at least one of receding motion, advancing motion, change in at least one of a size and position of said three-dimensional virtual reality object, blurring of said three-dimensional virtual reality object as perceivable by said subject and improving clarity of said three-dimensional virtual reality object as perceivable by said subject.

17. A method according to claim 10, and also comprising collimating light emanating from said display devices prior to said light arriving at said eyes of said subject.

* * * * *